(12) United States Patent
Kumakura et al.

(10) Patent No.: US 10,159,973 B2
(45) Date of Patent: Dec. 25, 2018

(54) SAMPLE LIQUID PREPARING APPARATUS, TEST KIT, AND SAMPLE LIQUID PREPARING METHOD

(71) Applicant: Toshiba Medical Systems Corporation, Otawara (JP)

(72) Inventors: Masahiro Kumakura, Otawara (JP); Shoichi Kanayama, Otawara (JP); Motoji Haragashira, Utsunomiya (JP); Asuka Hirano, Nasushiobara (JP); Dylann Ceriani, Vista, CA (US); Bob Eisele, Vista, CA (US)

(73) Assignee: Toshiba Medical Systems Corporation, Otawara-shi (JP)

( * ) Notice: Subject to any disclaimer, the term of this patent is extended or adjusted under 35 U.S.C. 154(b) by 167 days.

(21) Appl. No.: 15/253,328

(22) Filed: Aug. 31, 2016

(65) Prior Publication Data

US 2018/0056289 A1 Mar. 1, 2018

(51) Int. Cl.
*B01L 3/00* (2006.01)
*B01L 3/02* (2006.01)
*G01N 1/38* (2006.01)

(52) U.S. Cl.
CPC ............ *B01L 3/502* (2013.01); *B01L 3/0217* (2013.01); *B01L 2200/0689* (2013.01); *B01L 2300/042* (2013.01); *B01L 2300/069* (2013.01); *B01L 2300/0681* (2013.01); *B01L 2300/0838* (2013.01); *B01L 2300/0867* (2013.01); *B01L 2300/123* (2013.01); *B01L 2400/0478* (2013.01); *G01N 1/38* (2013.01)

(58) Field of Classification Search
CPC .... B01L 3/502; B01L 3/50; B01L 3/00; B01L 2200/0689; B01L 2200/06; B01L 2300/042; B01L 2300/04; B01L 2300/00; G01N 1/38; G01N 1/28; G01N 1/00; A61B 5/150358; A61B 5/150007; A61B 5/15
USPC ............................ 422/400, 50, 430; 436/174
See application file for complete search history.

(56) References Cited

U.S. PATENT DOCUMENTS

| | | | |
|---|---|---|---|
| 6,468,474 B2* | 10/2002 | Bachand | A61B 10/0051 422/411 |
| 7,544,324 B2* | 6/2009 | Tung | A61B 10/0045 422/504 |
| 2005/0180882 A1* | 8/2005 | Tung | A61B 10/0045 422/504 |

(Continued)

FOREIGN PATENT DOCUMENTS

JP 2015-523894 8/2015

*Primary Examiner* — Christine T Mui
(74) *Attorney, Agent, or Firm* — Oblon, McClelland, Maier & Neustadt, L.L.P.

(57) ABSTRACT

A sample liquid preparing apparatus includes a first cylinder portion, a cap portion, and a liquid preparation vessel. The first cylinder portion has a first to-be-fixed portion and a second to-be-fixed portion. The first cylinder portion accommodates a first plug and a second plug. A liquid is sealed between these plugs. The cap portion includes a plunger portion to push the second plug and a first fixing portion to limit the plunger portion from pushing the second plug by fixing the first to-be-fixed portion. The liquid preparation vessel includes a second cylinder portion whose internal space is pressed by the first cylinder portion and a second fixing portion to limit the first cylinder portion from pushing by fixing the second to-be-fixed portion.

17 Claims, 23 Drawing Sheets

(56) References Cited

U.S. PATENT DOCUMENTS

2015/0182156 A1  7/2015  Engbersen et al.

* cited by examiner

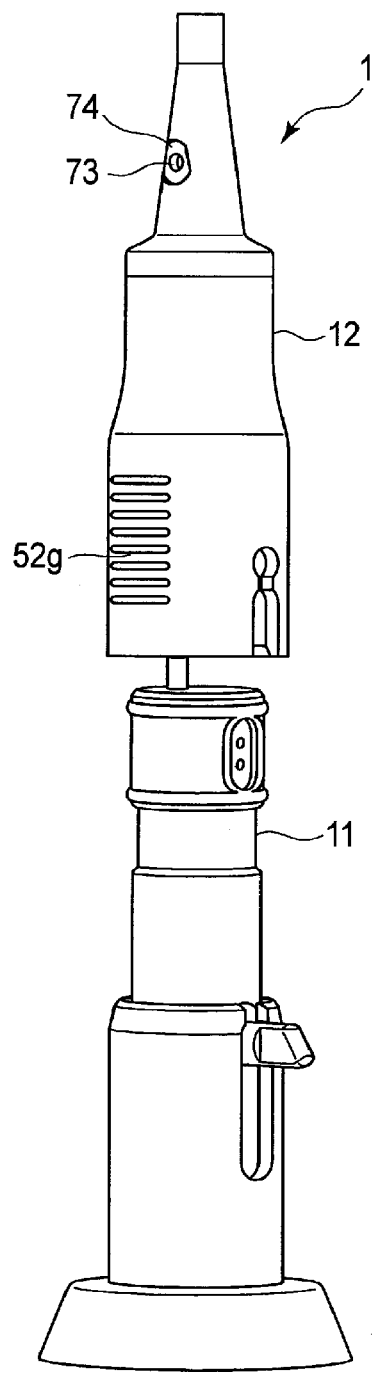
F I G. 1

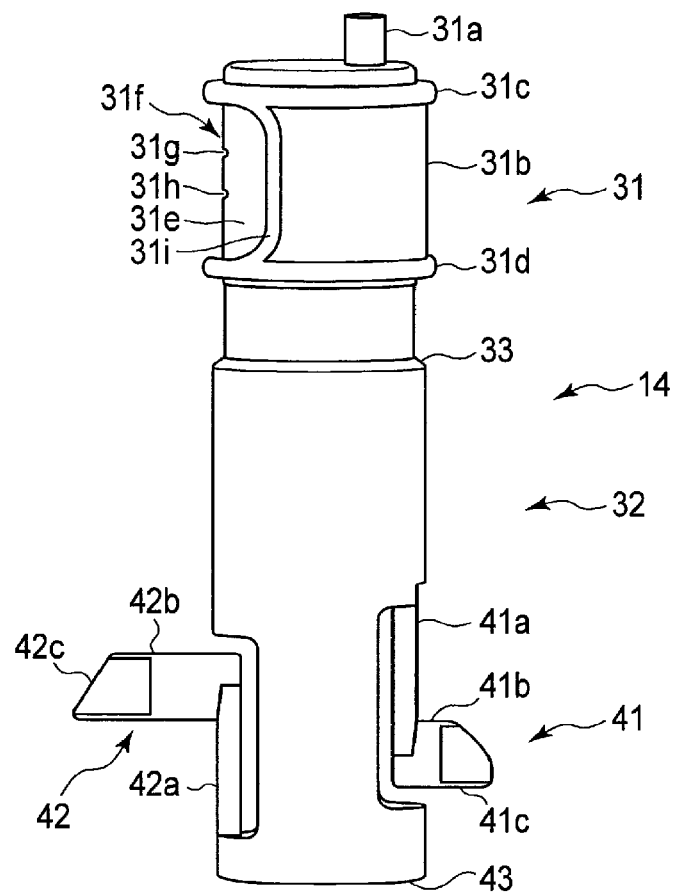
F I G. 4

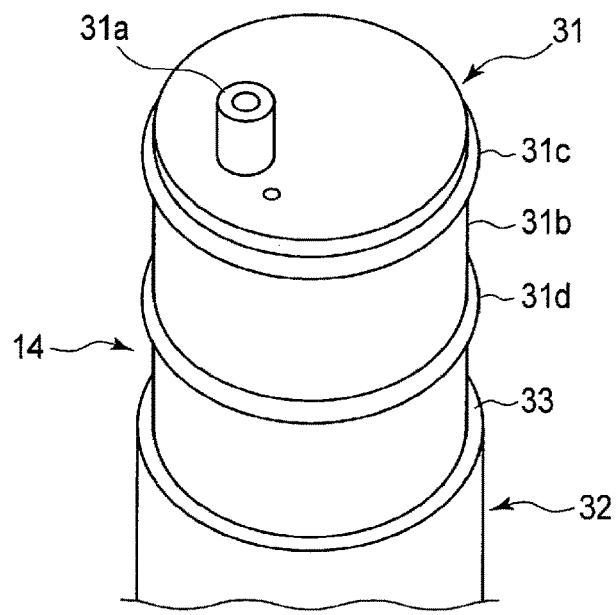
F I G. 5
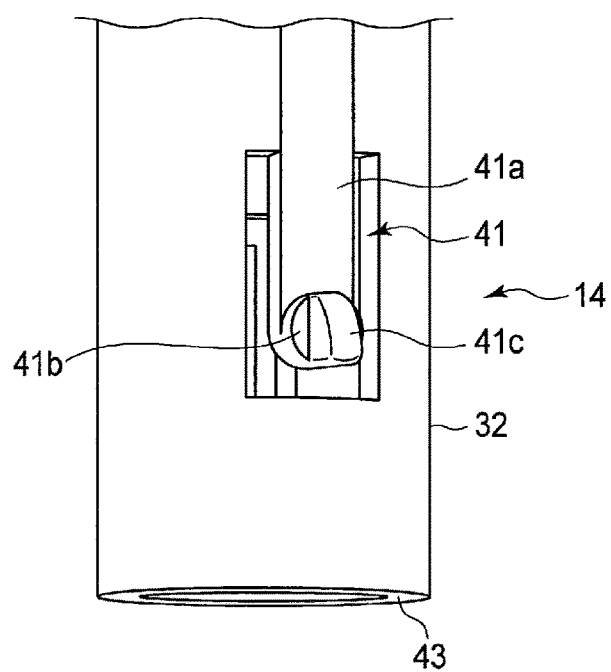
F I G. 6

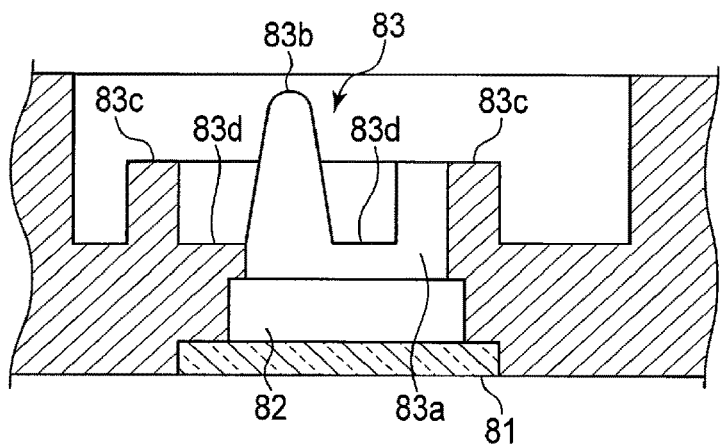
F I G. 11
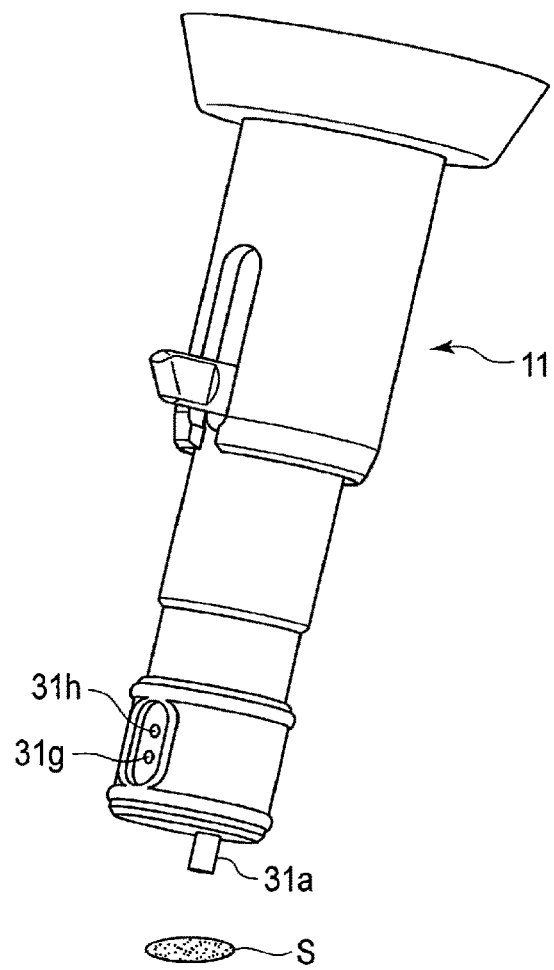
F I G. 12

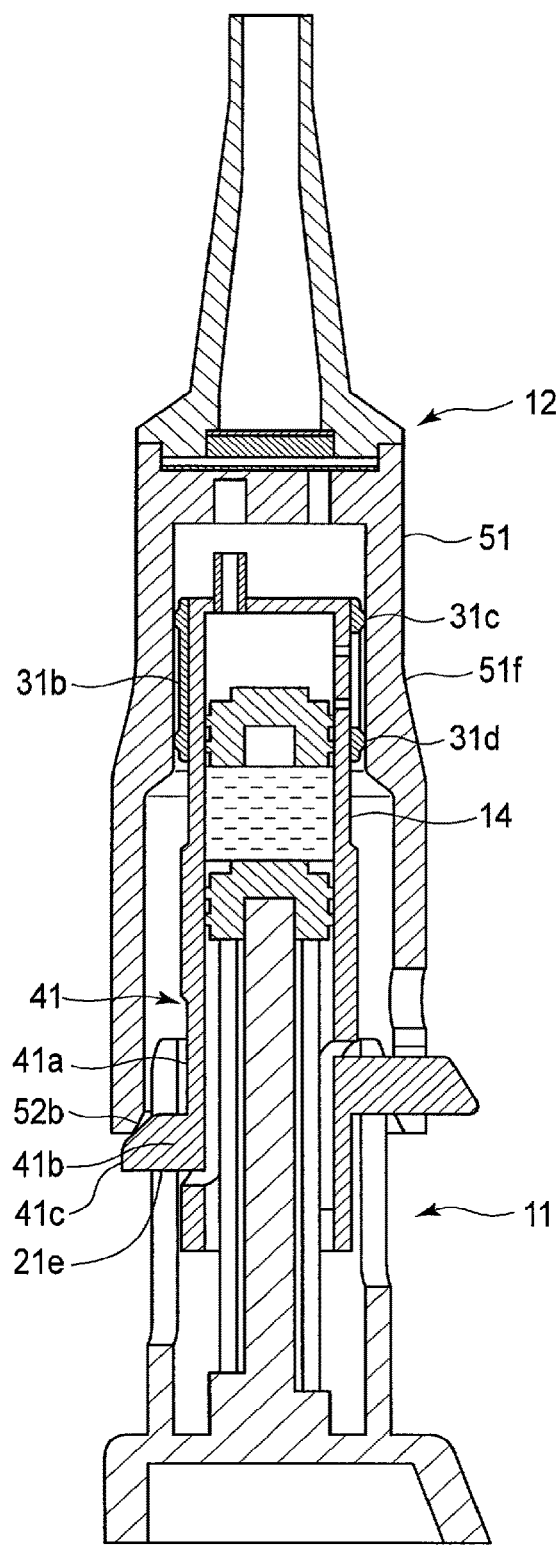
F I G. 14

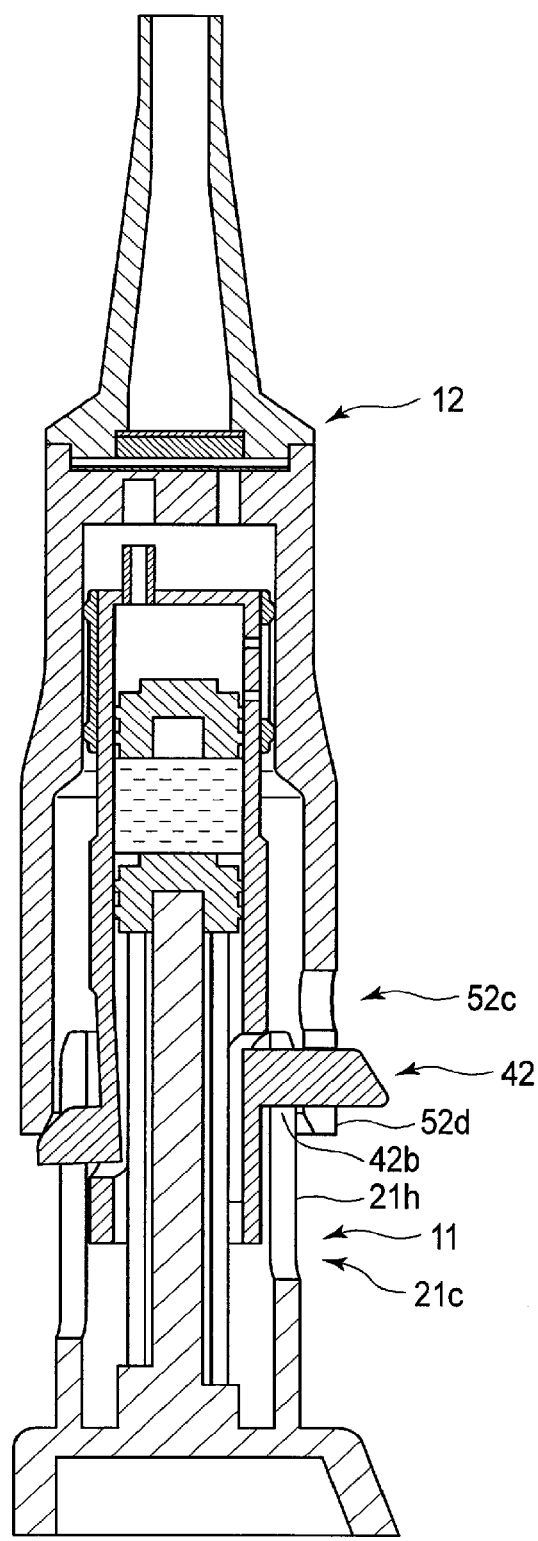
F I G. 15

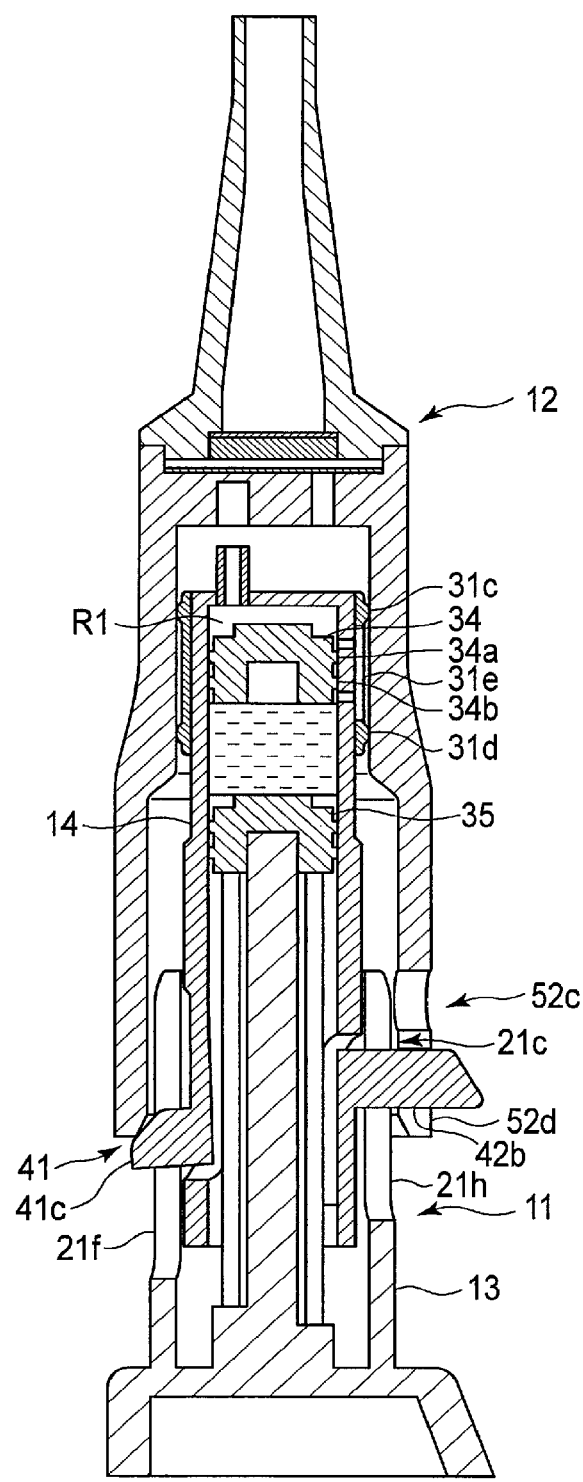
F I G. 17

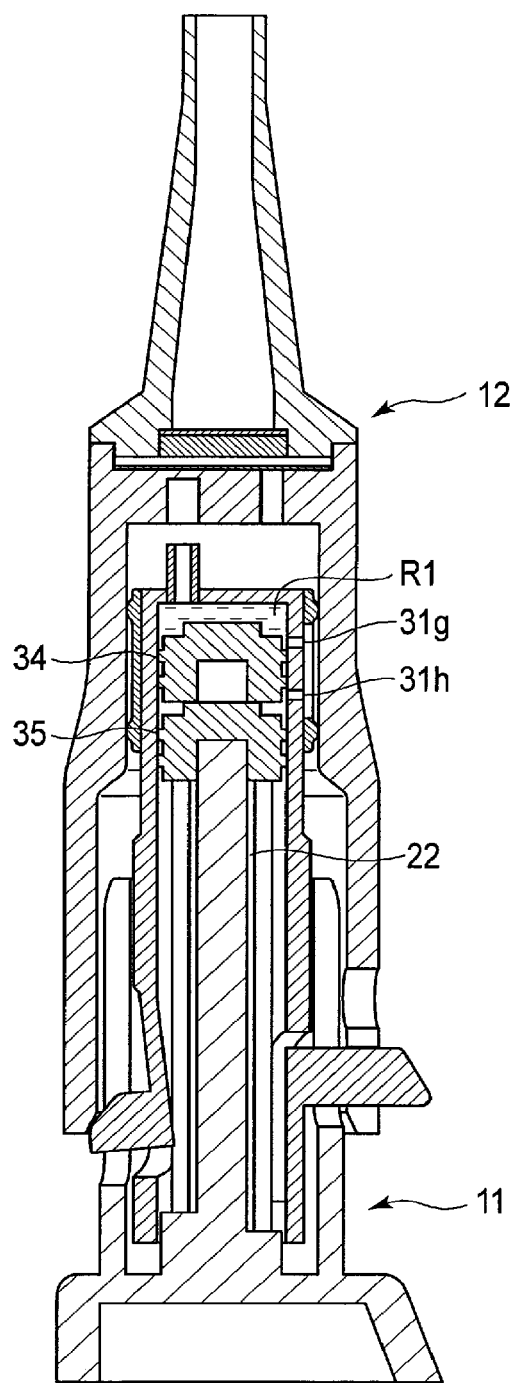
F I G. 18

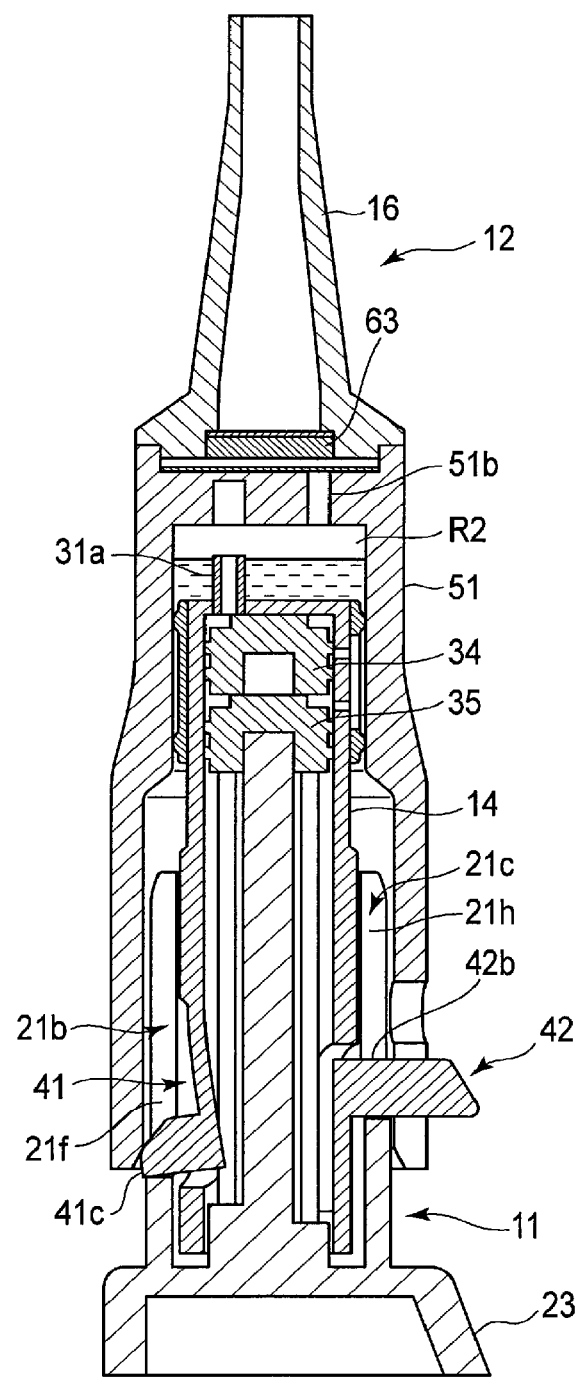
F I G. 19

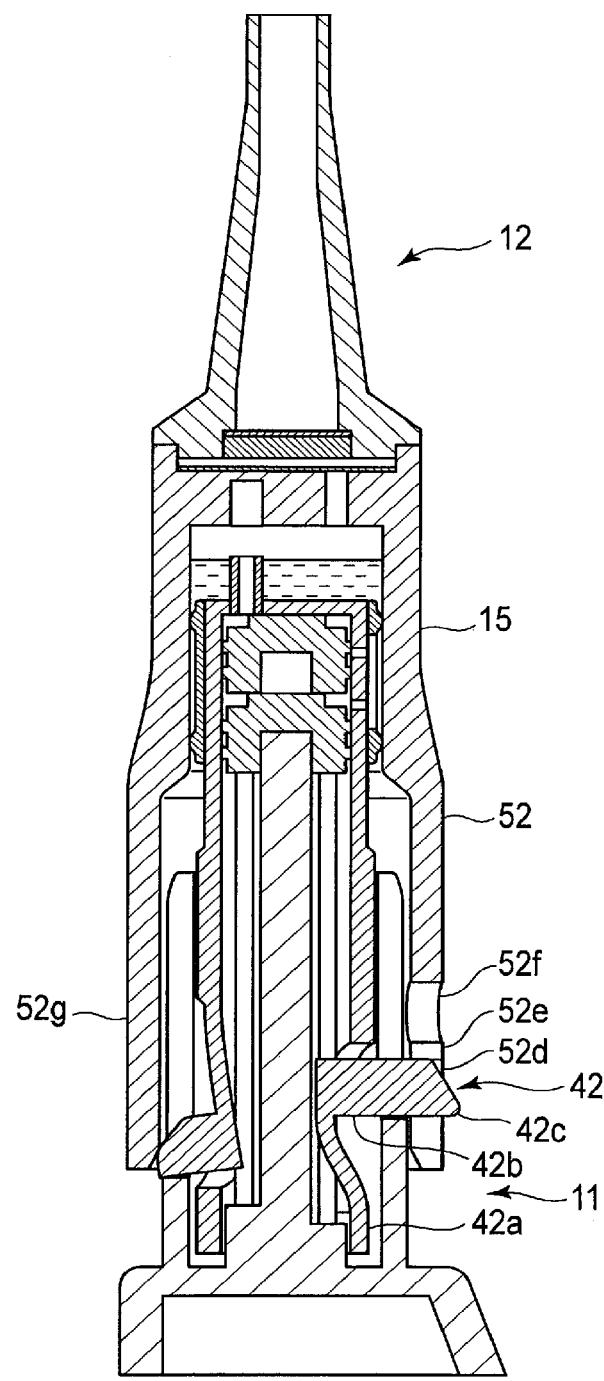
F I G. 20

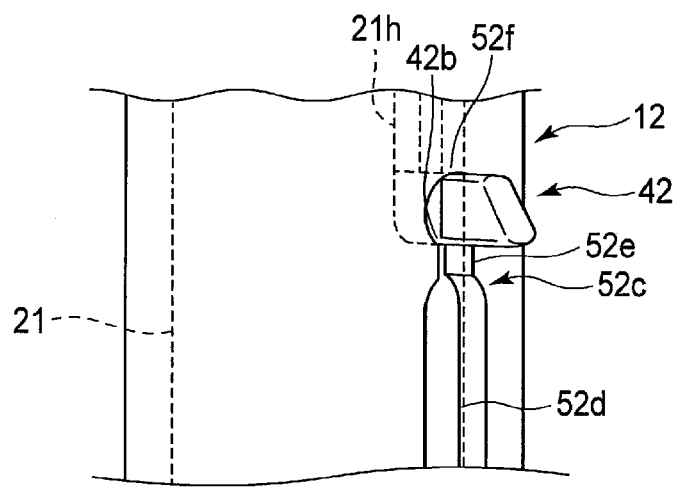
F I G. 22

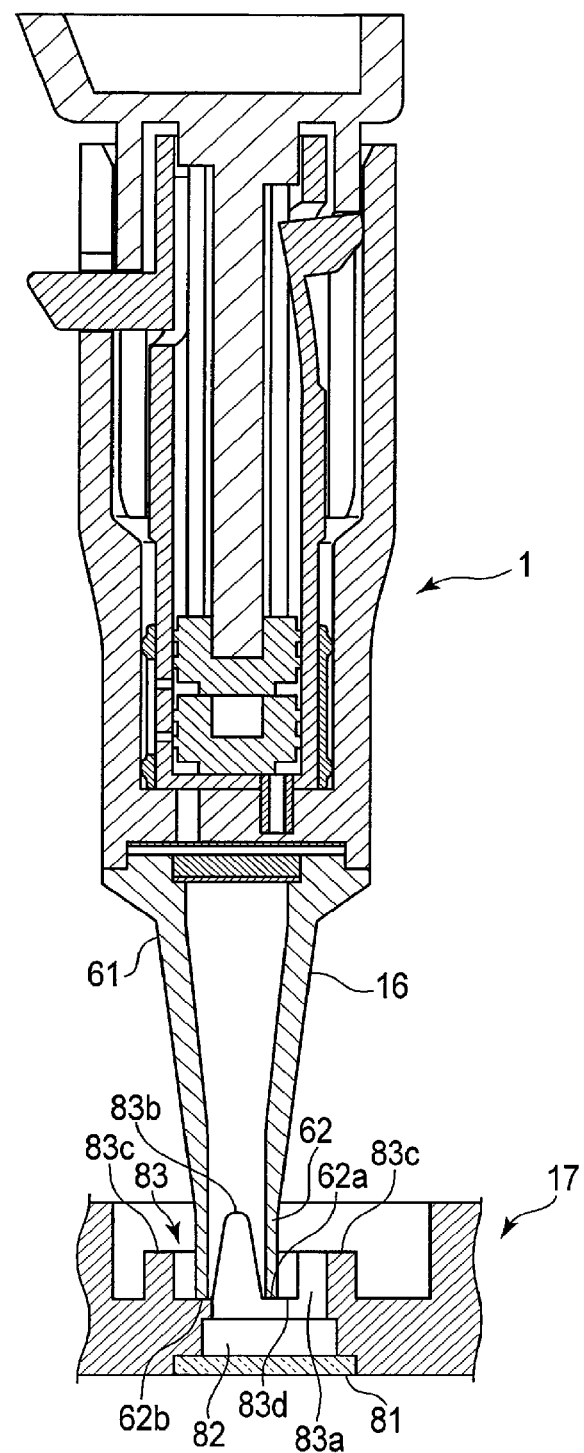
F I G. 23

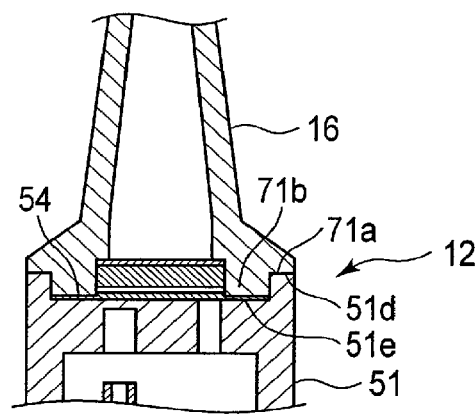
F I G. 24
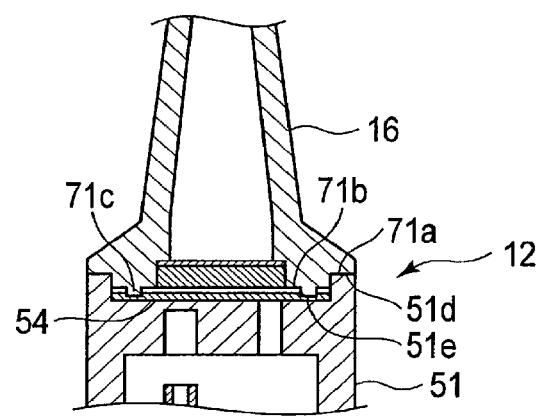
F I G. 25

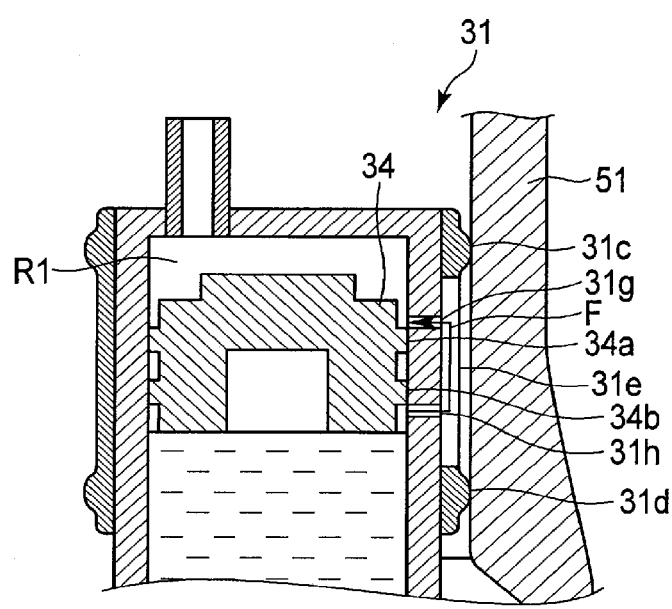
F I G. 29

SAMPLE LIQUID PREPARING APPARATUS, TEST KIT, AND SAMPLE LIQUID PREPARING METHOD

FIELD

Embodiments described herein relate generally to a sample liquid preparing apparatus, a test kit, and a sample liquid preparing method.

BACKGROUND

Recently, there has been a test proposed for determining the presence/absence of a suspected substance in blood by using a test kit including a sample liquid preparing apparatus and a test cartridge. A conventional sample liquid preparing apparatus collects, for example, whole blood as a sample from the human body. Upon external application of a predetermined force, the sample liquid preparing apparatus injects a predetermined amount of sample process liquid stored inside the unit into a test cartridge while mixing it with a collected sample. The test cartridge includes a filter in which a first reagent has been adsorbed, which reacts with a liquid mixture of a sample process liquid and a sample and a strip into which a second reagent has been adsorbed, which reacts with the reaction liquid which has reacted with the liquid mixture and the first reagent. When the liquid mixture is injected into the test cartridge, the liquid mixture passes through the filter provided in the test cartridge. With this operation, the first reagent elutes into the liquid mixture. The reaction liquid which has reacted with the liquid mixture and the first reagent moves on the strip by a capillary action. With this operation, the second reagent elutes into the reaction liquid.

In the above arrangement, however, the concentration of a sample contained in a liquid mixture injected from the sample liquid preparing apparatus is not consistent between the early and final phases of injection. That is, since a large amount of sample elutes into the sample process liquid in the early phase of injection, the concentration of the sample is high in the early phase of injection and gradually decreases toward the final phase. In addition, in the test cartridge, the amount of first reagent eluting into the liquid mixture is large in the early phase in which the liquid mixture passes through the filter, and gradually decreases toward the final phase of the passage. When the liquid mixture is not uniformly mixed and the first reagent does not uniformly elute into the liquid mixture as described above, a correct test result may not be obtained.

BRIEF DESCRIPTION OF THE DRAWING

FIG. 1 is a perspective view showing the arrangement of a sample liquid preparing apparatus according to an embodiment.

FIG. 4 is a front view showing the arrangement of a first cylinder portion shown in FIG. 2.

FIG. 5 is a perspective view showing the arrangement of the front end portion of the first cylinder portion shown in FIG. 4.

FIG. 6 is a perspective view showing the arrangement of the first to-be-fixed portion of the first cylinder portion shown in FIG. 4.

FIG. 11 is a sectional view showing the arrangement of a test cartridge shown in FIG. 10.

FIG. 12 is a perspective view showing a case in which the sample collection unit collects a sample.

FIG. 14 is a sectional view showing a case in which the first to-be-fixed portion of the first cylinder portion comes into contact with the third opening portion of the liquid preparation vessel.

FIG. 15 is a sectional view showing a case in which the second to-be-fixed portion of the first cylinder portion is fixed by the third guide portion of the liquid preparation vessel.

FIG. 17 is a sectional view showing a case in which a flow channel in the first cylinder portion is open.

FIG. 18 is a sectional view showing a case in which first and second plugs accommodated in the first cylinder portion abut against each other.

FIG. 19 is a sectional view showing a case in which the first plug abuts against the inner end face of the first cylinder portion.

FIG. 20 is a sectional view showing a case in which the second to-be-fixed portion of the first cylinder portion is released from the third guide portion of the liquid preparation vessel.

FIG. 22 is an enlarged view of the second to-be-fixed portion and the third guide portion shown in FIG. 21.

FIG. 23 is a sectional view showing a case in which a reaction liquid generated by the sample liquid preparing apparatus shown in FIG. 21 is dispensed into a test cartridge.

FIG. 24 is a sectional view showing another example of attaching a film shown in FIG. 9.

FIG. 25 is a sectional view showing still another example of attaching the film shown in FIG. 9.

FIG. 29 is a sectional view showing the arrangement of the sample liquid preparing unit shown in FIG. 17.

DETAILED DESCRIPTION

In general, according to one embodiment, a sample liquid preparing apparatus includes a first cylinder portion, a cap portion, and a liquid preparation vessel. The first cylinder portion has a first to-be-fixed portion and a second to-befixed portion. The first cylinder portion accommodates a first plug and a second plug. A liquid is sealed between the first plug and the second plug. The cap portion is provided to accommodate the first cylinder portion. The cap portion includes a plunger portion and a first fixing portion. The plunger portion pushes the second plug. The first fixing portion limits the plunger portion from pushing the second plug by fixing the first to-be-fixed portion. The liquid preparation vessel is provided to accommodate the first cylinder portion and the cap portion. The liquid preparation vessel includes a second cylinder portion and a second fixing portion. An internal space of the second cylinder portion is sealed by the first cylinder portion. The second fixing portion limits the first cylinder portion from pushing by fixing the second to-be-fixed portion.

The embodiments will now be described with reference to the accompanying drawings.

Figure 2:
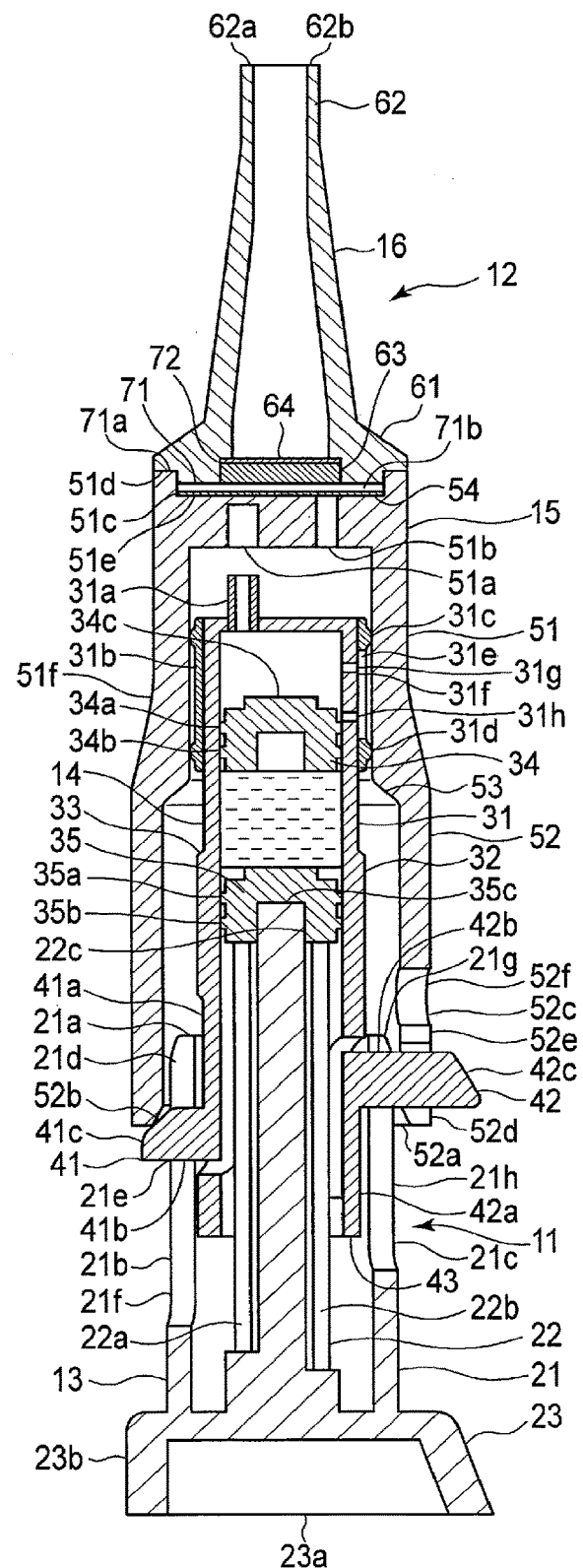
FIG. 2 is a sectional view showing the arrangement of the sample liquid preparing apparatus shown in FIG. 1.
Figure 3:
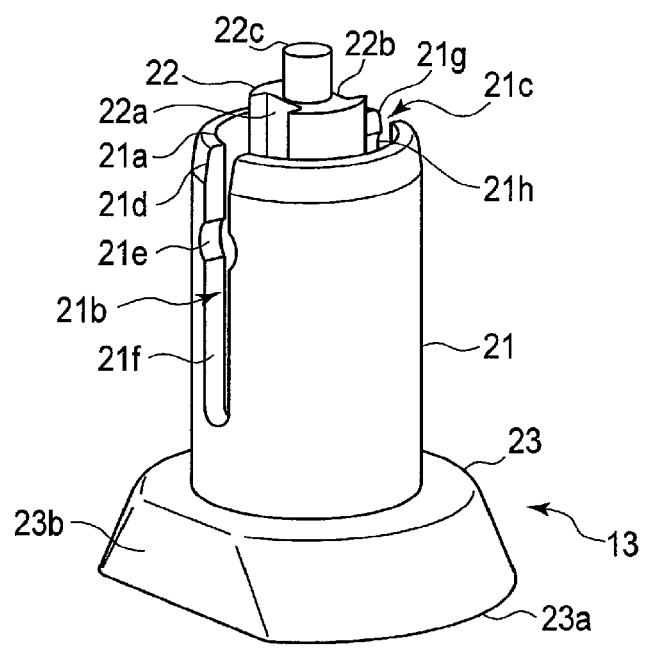
FIG. 3 is a perspective view showing the arrangement of a cap portion shown in FIG. 2.
Figure 7:
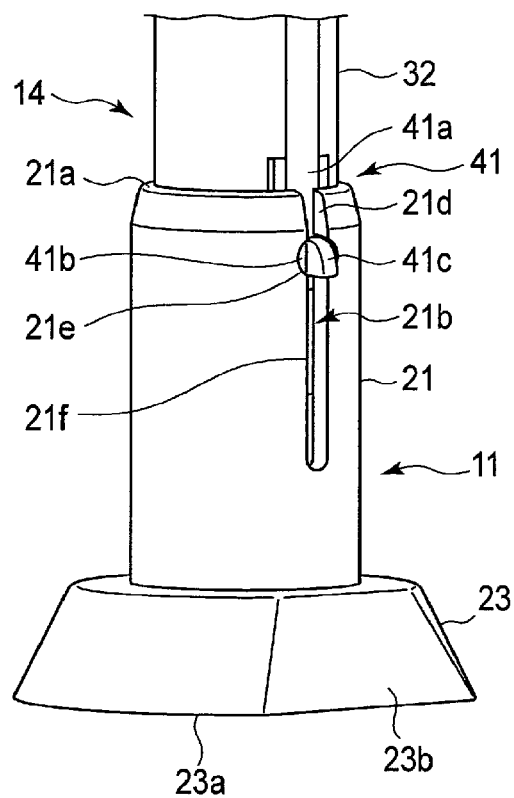
FIG. 7 is a perspective view showing the arrangement of a sample collection unit shown in FIG. 2.
Figure 8:
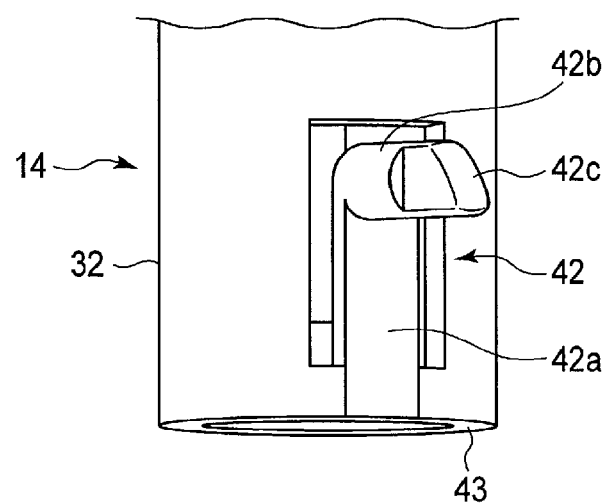
FIG. 8 is a perspective view showing the arrangement of the second to-be-fixed portion of the first cylinder portion shown in FIG. 4.
Figure 9:
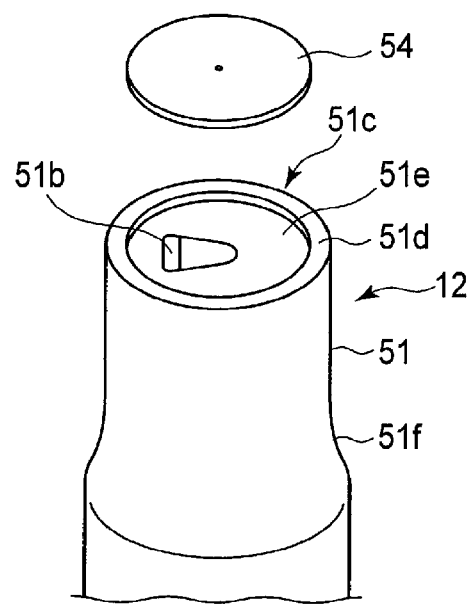
FIG. 9 is a perspective view showing the arrangement of a liquid preparation vessel shown in FIG. 2.

FIG. 1 is a perspective view showing the arrangement of a sample liquid preparing apparatus 1 according to this embodiment. FIG. 2 is a sectional view showing the arrangement of the sample liquid preparing apparatus 1. FIG. 3 is a perspective view showing the arrangement of a cap portion 13 used by a sample collection unit 11 of the sample liquid preparing apparatus 1. FIG. 4 is a front view showing the arrangement of a first cylinder portion 14 used by the sample collection unit 11. FIG. 5 is a perspective view showing the arrangement of a front end portion 31 of the first cylinder portion 14. FIG. 6 is a perspective view showing the arrangement of a first to-be-fixed portion 41 of the first cylinder portion 14. FIG. 7 is a perspective view showing the arrangement of the sample collection unit 11. FIG. 8 is a perspective view showing the arrangement of a second to-be-fixed portion 42 of the first cylinder portion 14. FIG. 9 is a perspective view showing the arrangement of a liquid preparation vessel 15 used by a sample liquid preparing unit 12 of the sample liquid preparing apparatus 1.

As shown in FIGS. 1 and 2, the sample liquid preparing apparatus 1 includes the sample collection unit 11 and the sample liquid preparing unit 12. The front end of the sample collection unit 11 is formed to be able to collect a sample from a subject. For example, a body fluid such as whole blood is assumed to be a sample. As shown in FIG. 1, the sample liquid preparing unit 12 is sheathed onto the sample collection unit 11 from its front end side and accommodates the sample collection unit 11.

As shown FIGS. 1 and 2, the sample collection unit 11 includes the first cylinder portion 14 which stores a sample process liquid to be mixed with a collected sample and the cap portion 13 functioning as a plunger with respect to the first cylinder portion 14. A sample processing liquid is, for example, a buffer liquid. The cap portion 13 and the first cylinder portion 14 are formed by using a thermosetting resin material such as polypropylene (PP), polyphenylene sulfide (PPS), high-density polyethylene (HDPE), polystyrene (PS), polybutylene terephthalate (PBT), polyacetal (POM), polyethylene naphthalate (PEN) polyethylene terephthalate (PET), polycarbonate (PC), or polyether ether ketone (PEEK).

As shown in FIGS. 2 and 3, the cap portion 13 includes a cylindrical outer portion 21, a plunger portion 22 formed along the axial direction of the outer portion 21, and a pedestal portion 23 integrally formed with one end of the outer portion 21 and one end of the plunger portion 22.

The outer portion 21 is formed to be able to accommodate a rear end portion 32 of the first cylinder portion 14 through a first opening portion 21a. More specifically, the outer portion 21 is formed to have an inner diameter slightly larger than the outer diameter of the rear end portion 32. In addition, the outer portion 21 is formed to be able to limit the movement of the first cylinder portion 14 in the axial direction of the outer portion 21 and to allow the first cylinder portion 14 to move along the axis direction of the outer portion 21.

The outer portion 21 includes a first guide portion 21b and a second guide portion 21c. The first guide portion 21b is a slit extending along the axial direction of the outer portion 21. The first guide portion 21b includes a first slit portion 21d open to the first opening portion 21a, a first fixing portion 21e, and a second slit portion 21f. The first slit portion 21d is formed to allow a first to-be-guided portion 41c provided for the first to-be-fixed portion 41 of the rear end portion 32 of the first cylinder portion 14 to slide along the axial direction of the outer portion 21. More specifically, the first slit portion 21d is formed to have a width slightly larger than that of the first to-be-guided portion 41c.

The first fixing portion 21e is formed to be able to fix the first to-be-fixed portion 41 of the rear end portion 32 of the first cylinder portion 14. More specifically, the first fixing portion 21e is a circular through-hole having a diameter slightly larger than that of a first columnar portion 41b of the first to-be-fixed portion 41 and is provided on the pedestal portion 23 side so as to coincide with the first slit portion 21d. The first fixing portion 21e is a circular through-hole which increases a contact area with the first columnar portion 41b, thereby preventing the plunger portion 22 of the cap portion 13 from pushing a first plug 34 and a second plug 35 of the first cylinder portion 14 toward the front end portion 31. The position at which the first fixing portion 21e is formed is decided based on the position of the second plug 35 accommodated in the first cylinder portion 14.

The second slit portion 21f allows the first to-be-guided portion 41c provided for the first to-be-fixed portion 41 of the rear end portion 32 of the first cylinder portion 14 to slide along the axial direction of the outer portion 21. More specifically, the second slit portion 21f extends toward the pedestal portion 23 while interfacing with the first fixing portion 21e. The second slit portion 21f is formed to have a width slightly larger than that of the first to-be-guided portion 41c. The position of an end portion of the second slit portion 21f is decided based on a position which it can push the plunger portion 22 into the first cylinder portion 14.

The second guide portion 21c is a slit extending along the axial direction at a position 180 degrees from the first guide portion 21b through the axis of the outer portion 21. The second guide portion 21c includes a third slit portion 21g open to the first opening portion 21a and a fourth slit portion 21h extending to the pedestal portion 23 side while communicating with the third slit portion 21g. The third slit portion 21g is formed to allow a second to-be-guided portion 42c provided for the second to-be-fixed portion 42 of the rear end portion 32 of the first cylinder portion 14 to slide along the axial direction. More specifically, the third slit portion 21g is formed to have a width slightly larger than that of the second to-be-guided portion 42c.

The fourth slit portion 21h is formed to be able to limit the entrance of a second columnar portion 42b provided for the second to-be-fixed portion 42 of the rear end portion 32 of the first cylinder portion 14 into the third slit portion 21g and to allow the second columnar portion 42b to slide along the axial direction. More specifically, the portion of the fourth slit portion 21h which communicates with the third slit portion 21g is formed into a nearly semi-circular shape with a diameter slightly larger than that of the second columnar portion 42b. In addition, the fourth slit portion 21h is formed to have a width slightly larger than the diameter of the second columnar portion 42b. The fourth slit portion 21h is formed such that the position of the semi-circular shape is closer to the first opening portion 21a than the first fixing portion 21e by a predetermined distance. Furthermore, the fourth slit portion 21h is formed such that the position of the end portion on the pedestal portion 23 side is closer to the first opening portion 21a than the position of the end portion of the second slit portion 21f which is located on the pedestal portion 23 side by a predetermined distance.

The plunger portion 22 is formed to be able to be inserted into a second opening portion 43 of the first cylinder portion 14. The plunger portion 22 is formed into a columnar shape having a first groove portion 22a and a second groove portion 22b. The plunger portion 22 is formed to have an outer diameter slightly smaller than the inner diameter of the rear end portion 32 of the first cylinder portion 14.

The first groove portion 22a extends in the axial direction of the plunger portion 22 at a position facing the first guide portion 21b. The first groove portion 22a is formed to allow the first to-be-fixed portion 41 to move in the axial direction of the plunger portion 22 when a first beam portion 41a provided for the first to-be-fixed portion 41 of the rear end portion 32 of the first cylinder portion 14 flexes in the central direction. More specifically, the first groove portion 22a is formed to have a width slightly larger than that of the first beam portion 41a and also have a depth slightly larger than a distance by which the first to-be-guided portion 41c is pushed in the central direction.

The second groove portion 22b extends in the axial direction of the plunger portion 22 at a position facing the second guide portion 21c. The second groove portion 22b is formed to allow the second to-be-fixed portion 42 to move in the axial direction of the plunger portion 22 when a second beam portion 42a provided for the second to-be-fixed portion 42 of the rear end portion 32 of the first cylinder portion 14 flexes in the central direction. More specifically, the second groove portion 22b is formed to have a width slightly larger than that of the second beam portion 42a and have a depth slightly larger than a distance by which the second to-be-guided portion 42c is pushed in the central direction.

The plunger portion 22 has a core portion 22c on an end portion which abuts against the second plug 35. The core portion 22c is formed to be able to fit in a first hole portion 35c provided in the second plug 35. More specifically, the core portion 22c is formed to have an outer diameter almost equal to the inner diameter of the first hole portion 35c.

The pedestal portion 23 is integrally formed with the outer portion 21 and the plunger portion 22. The pedestal portion 23 is formed to allow the cap portion 13 to stand upright. More specifically, the pedestal portion 23 has a first planar portion 23a formed in a direction perpendicular to the axis of the outer portion 21 on the end portion on the other side on which the outer portion 21 and the plunger portion 22 are formed. The pedestal portion 23 has a second planar portion 23b formed along the axis of the outer portion 21 in almost the same direction in which the first guide portion 21b is formed. If the sample liquid preparing apparatus 1 is knocked over or is placed on the work surface, the second planar portion 23b can prevent the rotation of the sample liquid preparing apparatus 1.

As shown in FIGS. 2 and 4, the first cylinder portion 14 is a cylindrical member designed to have different, coaxial diameters and has an end face at one end. The first cylinder portion 14 is formed to be able to be inserted into the liquid preparation vessel 15 of the sample liquid preparing unit 12 and accommodated in the cap portion 13. More specifically, the first cylinder portion 14 includes, from its one end side towards the other end side, the front end portion 31 and the rear end portion 32.

The front end portion 31 has a capillary portion 31a formed into a cylindrical shape on an end face located on the same side as that of a second cylinder portion 51 provided for the liquid preparation vessel 15 of the sample liquid preparing unit 12. As shown in FIG. 5, the capillary portion 31a is formed at a position off-centered from the axis of the first cylinder portion 14, i.e., a position spaced apart from the axis of the first cylinder portion 14 by a predetermined distance. This improves the visibility of the front end of the capillary portion 31a when collecting a sample and allows easy recognition of the relative position between a sample position and the capillary portion 31a. The capillary portion 31a is also formed such that its center locates more apart from the axis of the first cylinder portion 14 than the outer circumferential surface of a cylindrical projection portion 34c (to be described later) of the first plug 34. In other words, the distance between the axis of the first cylinder portion 14 and the center of the capillary portion 31a is larger than the distance between the axis of the first cylinder portion 14 and the outer circumferential surface of the cylindrical projection portion 34c.

The inner diameter and length of the capillary portion 31a can be adjusted in accordance with the amount of sample to be collected. The capillary portion 31a may be formed from a transparent or semitransparent material. Forming the capillary portion 31a by using a transparent or semitransparent material improves the visibility when collecting a colored sample such as blood, and hence allows reliable collection of a predetermined amount of sample.

The front end portion 31 is formed to be able to function as a syringe with respect to the second cylinder portion 51 provided for the liquid preparation vessel 15 of the sample liquid preparing unit 12. More specifically, the front end portion 31 is formed to have an outer diameter smaller than the inner diameter of the second cylinder portion 51. In addition, the front end portion 31 has a sealing member 31b which is provided on its outer circumferential surface and abuts against the inner circumferential surface of the second cylinder portion 51 of the liquid preparation vessel 15. The sealing member 31b is formed by using an elastically deformable resin material, for example, a rubber based resin material such as ethylene propylene rubber (EPTE, PDM), nitrile rubber (NBR), fluoro-rubber (FKM), styrene-butadiene rubber (SBR), silicone rubber (VMQ), or chloroprene rubber (CR) or a synthetic resin material such as low-density polyethylene (LDPE), soft vinyl chloride (PVC), nylon (PA), polyurethane (PU), or TEFLON®.

The sealing member 31b is formed by over-molding. The sealing member 31b includes a first seal portion 31c provided on the front end portion 31 side and a second seal portion 31d provided on the rear end portion 32 side. The first seal portion 31c is an annular projection provided on the sealing member 31b. When the first cylinder portion 14 is inserted into the second cylinder portion 51 of the liquid preparation vessel 15, the first seal portion 31c partially elastically deforms to seal the gap between the outer circumferential surface of the front end portion 31 and the inner circumferential surface of the second cylinder portion 51. The second seal portion 31d is an annular projection provided on the sealing member 31b. When the first cylinder portion 14 is inserted into the second cylinder portion 51 of the liquid preparation vessel 15, the second seal portion 31d partially elastically deforms to seal the gap between the outer circumferential surface of the front end portion 31 and the inner circumferential surface of the second cylinder portion 51.

The sealing member 31b has a window portion 31e in almost the same direction in which the second to-be-fixed portion 42 provided on the rear end portion 32 is formed. The window portion 31e exposes the outer circumferential surface of the front end portion 31.

The front end portion 31 has a bypass portion 31f in the outer circumferential surface exposed by the window portion 31e. The bypass portion 31f has a first through-hole portion 31g and a second through-hole portion 31h which are formed side by side in the axial direction of the first cylinder portion 14. The first through-hole portion 31g is formed on the first seal portion 31c side. The second through-hole portion 31h is formed on the second seal portion 31d side. The first through-hole portion 31g and the second through-hole portion 31h are formed to allow, between them, a third seal portion 34a and a fourth seal portion 34b of the first plug 34 to be accommodated. The sealing member 31b has a bypass seal portion 31i surrounding the bypass portion 31f. The bypass seal portion 31i is an annular projection. When the first cylinder portion 14 is inserted into the second cylinder portion 51 of the prepared liquid vessel 15, the bypass seal portion 31i partially elastically deforms to seal the gap between the outer circumferential surface of the front end portion 31 and the inner circumferential surface of the second cylinder portion 51.

The rear end portion 32 is integrally formed with the front end portion 31 through a first corner portion 33 which is a chamfered portion provided in an annular shape. The rear end portion 32 is formed to have an outer diameter slightly larger than that of the front end portion 31. In addition, the rear end portion 32 is formed to have an inner diameter equal to that of the front end portion 31.

The rear end portion 32 is formed to be able to be accommodated in the cap portion 13. More specifically, the rear end portion 32 is formed to have an outer diameter smaller than the inner diameter of the outer portion 21 and have an inner diameter larger than the outer diameter of the plunger portion 22. The rear end portion 32 is also formed such that the length from the second opening portion 43 of the rear end portion 32 to the end portion on the rear end portion 32 side of the first corner portion 33 is almost equal to the length from the first opening portion 21a of the outer portion 21 to the principal surface on the outer portion 21 side of the pedestal portion 23.

The rear end portion 32 has the first to-be-fixed portion 41 and the second to-be-fixed portion 42 in a direction opposite each other through the axis of the first cylinder portion 14. The first to-be-fixed portion 41 is formed to be able to be fixed to the first fixing portion 21e of the cap portion 13. More specifically, as shown in FIG. 6, the first to-be-fixed portion 41 has the first beam portion 41a, the first columnar portion 41b, and the first to-be-guided portion 41c.

The first beam portion 41a is a cantilever beam extending from the front end portion 31 side in the direction of the rear end portion 32 along the axis of the first cylinder portion 14. The first columnar portion 41b is a columnar projection formed on the front end of the first beam portion 41a. The first columnar portion 41b is formed such that the height from the surface of the first beam portion 41a is slightly larger than the thickness of the outer portion 21 of the cap portion 13. The position at which the first columnar portion 41b is formed is decided based on the position of the second plug 35 accommodated in the first cylinder portion 14.

The first to-be-guided portion 41c is a projection formed on the top portion of the first columnar portion 41b. The first to-be-guided portion 41c is formed to have a constant width in the circumferential direction of the rear end portion 32. In addition, the first to-be-guided portion 41c is formed such that the height of the first columnar portion 41b in the axial direction gradually increases from the front end portion 31 side to the rear end portion 32 side. Furthermore, the first to-be-guided portion 41c is formed such that the incremental gradient of the height is gradually reduced from the front end portion 31 side to the rear end portion 32 side. In other words, the top portion of the first to-be-guided portion 41c, that is, a portion which receives a stress from the inner wall of the liquid preparation vessel 15 (to be described later), has a round shape. This can prevent the first to-be-guided portion 41c from being caught by the inner wall of the liquid preparation vessel 15 when the sample collection unit 11 is accommodated in the sample liquid preparing unit 12. When the first cylinder portion 14 is accommodated in the cap portion 13 and the first columnar portion 41b is fixed by the first fixing portion 21e, the first to-be-guided portion 41c protrudes from the surface of the outer portion 21, as shown in FIG. 7.

The second to-be-fixed portion 42 is formed to be able to be fixed to an end portion of a fifth slit portion 52d and a terminal fixing portion 52f provided in a first accommodation portion 52 of the liquid preparation vessel 15 of the sample liquid preparing unit 12. More specifically, as shown in FIG. 8, the second to-be-fixed portion 42 has the second beam portion 42a, the second columnar portion 42b, and the second to-be-guided portion 42c.

The second beam portion 42a is a cantilever beam extending from the rear end portion 32 side in the direction of the front end portion 31 along the axis of the first cylinder portion 14. The second columnar portion 42b is a columnar projection formed on the front end of the second beam portion 42a. The second columnar portion 42b is formed such that the height from the surface of the second beam portion 42a is slightly larger than the sum of the thickness of the outer portion 21 of the cap portion 13 and the thickness of the first accommodation portion 52 of the liquid preparation vessel 15. The second columnar portion 42b is formed such that its position is closer to the front end portion 31 than the first columnar portion 41b of the first to-be-fixed portion 41 by a predetermined distance.

The second to-be-guided portion 42c is a projection formed on the top portion of the second columnar portion 42b. The second to-be-guided portion 42c is formed to have a constant width in the circumferential direction of the rear end portion 32. In addition, the second to-be-guided portion 42c is formed such that the height in the axial direction of the second columnar portion 42b gradually increases from the front end portion 31 side to the rear end portion 32 side.

The first cylinder portion 14 receives inside the first plug 34 and the second plug 35 which are formed from an elastically deformable resin material. The first plug 34 is arranged on the front end portion 31 side. The second plug 35 is arranged on the rear end portion 32 side. The first plug 34 and the second plug 35 are formed to be able to seal a sample process liquid between them to store the liquid in the first cylinder portion 14. More specifically, the first plug 34 includes a third seal portion 34a provided on the front end portion 31 side and a fourth seal portion 34b provided on the rear end portion 32 side. The third seal portion 34a and the fourth seal portion 34b are annular projections provided on the first plug 34. The third seal portion 34a and the fourth seal portion 34b abut against the inner circumferential surface of the first cylinder portion 14 and partially elastically deform to seal the gap between the inner circumferential surface of the first cylinder portion 14 and the first plug 34. Also, the first plug 34 includes the cylindrical projection portion 34c at its end face on the front end side of the first cylinder portion 14.

The second plug 35 includes a fifth seal portion 35a provided on the front end portion 31 side and a sixth seal portion 35b provided on the rear end portion 32 side. The fifth seal portion 35a and the sixth seal portion 35b are annular projections provided on the second plug 35. The fifth seal portion 35a and the sixth seal portion 35b abut against the inner circumferential surface of the first cylinder portion 14 and partially elastically deform to seal the gap between the inner circumferential surface of the first cylinder portion 14 and the second plug 35. The first cylinder portion 14 seals a sample process liquid in the sealed space formed between its inner circumferential surface and the first and second plugs 34 and 35. The position of the first plug 34 and the position of the second plug 35 are decided based on the mixing ratio (dilution ratio) between a sample and a sample process liquid.

The second plug 35 has, in the end face on the rear end portion 32 side, the first hole portion 35c into which the core portion 22c of the plunger portion 22 can be inserted. Inserting the high-rigidity core portion 22c in the second plug 35 can prevent the buckling and misalignment of the second plug 35. This increases the pressure on the inner circumferential surface of the front end portion 31 and makes it possible to prevent the leakage of a sample process liquid stored between the first plug 34 and the second plug 35.

As shown in FIGS. 1 and 2, the sample liquid preparing unit 12 includes the liquid preparation vessel 15 which prepares a sample collected by the sample collection unit 11 and a nozzle 16 which discharges a prepared solution. A thermosetting resin material is used for the liquid preparation vessel 15 and the nozzle 16.

The liquid preparation vessel 15 is formed to be able to accommodate the sample collection unit 11. As shown in FIG. 2, the liquid preparation vessel 15 has the second cylinder portion 51 and the first accommodation portion 52 integrally formed with each other. The liquid preparation vessel 15 includes a second corner portion 53 between the second cylinder portion 51 and the first accommodation portion 52. The second corner portion 53 is chamfered portion provided in an annular shape on the inner circumferential surface of the liquid preparation vessel 15.

The second cylinder portion 51 is a cylindrical member having an end face at one end, and is formed to allow the first cylinder portion 14 to be inserted inside. More specifically, the second cylinder portion 51 is formed to have an inner diameter slightly larger than the outer diameter of the first cylinder portion 14. The gap between the inner circumferential surface of the second cylinder portion 51 and the outer circumferential surface of the first cylinder portion 14 is sealed by the first seal portion 31c and the second seal portion 31d of the sealing member 31b.

The second cylinder portion 51 has a second hole portion 51a, which can accommodate the capillary portion 31a, at a position facing the capillary portion 31a of the first cylinder portion 14. More specifically, the second hole portion 51a is formed to have an inner diameter slightly larger than the outer diameter of the capillary portion 31a. In addition, the second hole portion 51a is formed to have a depth slightly larger than the length from the end face of the first cylinder portion 14 to the front end of the capillary portion 31a. The second cylinder portion 51 has a third through-hole portion 51b in the end face in which the second hole portion 51a is formed. The third through-hole portion 51b is a slit-like through-hole portion formed at a position facing the capillary portion 31a through the axis of the first cylinder portion 14. The third through-hole portion 51b serves as a flow channel along which a sample liquid mixture obtained by mixing a sample with a sample process liquid is made to flow from the liquid preparation vessel 15 to the nozzle 16.

The second cylinder portion 51 includes a to-be-connected portion 51c in the end of the nozzle 16 side. The to-be-connected portion 51c is formed to be able to be fitted to a connection portion 71 of the nozzle 16. More specifically, as shown in FIG. 9, the to-be-connected portion 51c includes a first edge portion 51d protruding in an annular form and a recess portion 51e. The recess portion 51e is formed to have an inner diameter almost equal to the outer diameter of a projection portion 71b provided on the connection port 71. The recess portion 51e is fitted on a projection portion 71b of the connection port 71. The principal surface of the first edge portion 51d is bonded to the principal surface of a second edge portion 71a provided on the connection port 71 by a technique such as ultrasonic welding, solvent bonding, or heat welding. This makes it possible to prevent the leakage of a fluid from the connecting portion between the liquid preparation vessel 15 and the nozzle 16.

The second cylinder portion 51 may has a film 54 on the recess portion 51e so as to cover the third through-hole portion 51b. More specifically, the film 54 is formed to have a diameter almost equal to the inner diameter of the recess portion 51e. An elastically deformable resin material may be used for the film 54. The film 54 has an edge portion coated with an adhesive agent in an annular form and is bonded to the recess portion 51e with the edge portion coated with the adhesive agent. Note that if the adhesive agent may influence a reaction system, the film 54 may be placed on the surface of the recess portion 51e, and the edge portion of the film 54 may be ultrasonically welded to the recess portion 51e in an annular form. The film 54 may has a small hole at a predetermined position excluding the edge portion bonded to the recess portion 51e.

The second cylinder portion 51 has a first grip portion 51f at part of the outer circumferential surface. The second cylinder portion 51 is formed to have an outer diameter smaller than that of the first accommodation portion 52. The first grip portion 51f is formed such that the outer diameter of the second cylinder portion 51 increases toward the first accommodation portion 52 up to the outer diameter of the first accommodation portion 52, and the incremental gradient of the outer diameter increases toward the first accommodation portion 52.

The first accommodation portion 52 is formed to be able to accommodate the outer portion 21 of the cap portion 13 through a third opening portion 52a. More specifically, the first accommodation portion 52 is formed to have an inner diameter larger than the outer diameter of the outer portion 21. In addition, the first accommodation portion 52 is formed such that the length from the third opening portion 52a to the end face of the second corner portion 53 which is located on the first accommodation portion 52 side is almost equal to the length from the first opening portion 21a of the outer portion 21 to the principal surface of the pedestal portion 23 which is located on the outer portion 21 side.

The first accommodation portion 52 has a tapered portion 52b on an edge portion of the third opening portion 52a which is located on the inner surface side. The tapered portion 52*b* is formed in an annular shape on the edge portion of the third opening portion 52*a* which is located on the inner surface side. Note that the tapered portion 52*b* may be formed on part of the edge portion, e.g., at a position facing a third guide portion 52*c* of the first accommodation portion 52 through the axis of the liquid preparation vessel 15, so as to have a predetermined width.

The first accommodation portion 52 is designed to allow the sample collection unit 11 to move along the axial direction of the liquid preparation vessel 15 while limiting the movement of the plugs 34 and 35 within the sample collection unit 11. More specifically, the first accommodation portion 52 includes the third guide portion 52*c*. The third guide portion 52*c* is a slit extending along the axial direction of the liquid preparation vessel 15. The third guide portion 52*c* has the fifth slit portion 52*d* open to the third opening portion 52*a*, a sixth slit portion 52*e*, and the terminal fixing portion 52*f*.

The fifth slit portion 52*d* is formed to allow the second columnar portion 42*b* provided for the second to-be-fixed portion 42 of the rear end portion 32 of the first cylinder portion 14 to slide along the axial direction and limit the entrance of the second columnar portion 42*b* into the sixth slit portion 52*e*. More specifically, the fifth slit portion 52*d* is formed to have a width slightly larger than the diameter of the second columnar portion 42*b*. In addition, the fifth slit portion 52*d* is formed such that its interface portion with the sixth slit portion 52*e* has a nearly semi-circular shape with a diameter slightly larger than that of the second columnar portion 42*b*.

The sixth slit portion 52*e* is formed to allow the second to-be-guided portion 42*c* provided for the second to-be-fixed portion 42 of the rear end portion 32 of the first cylinder portion 14 to slide along the axial direction. More specifically, the sixth slit portion 52*e* extends toward the second cylinder portion 51 while communicating with the fifth slit portion 52*d*. The sixth slit portion 52*e* is formed to have a width slightly larger than that of the second to-be-guided portion 42*c*.

The terminal fixing portion 52*f* is formed to be able to fix the second to-be-fixed portion 42 of the rear end portion 32 of the first cylinder portion 14. More specifically, the terminal fixing portion 52*f* is a circular through-hole which has a diameter slightly larger than that of the second columnar portion 42*b* of the second to-be-fixed portion 42 and is provided on the second cylinder portion 51 side while communicating with the sixth slit portion 52*e*. The relative positions of the end portions of the first columnar portion 41*b* of the first to-be-fixed portion 41, the second columnar portion 42*b* of the second to-be-fixed portion 42, and the fifth slit portion 52*d* of the third guide portion 52*c* are decided upon decision of the positions of the first plug 34 and the second plug 35.

A second grip portion 52*g* is formed on the outer circumferential surface of the first accommodation portion 52.

The nozzle 16 is a cylindrical member formed to coaxially have different diameters, with one end being bonded to the liquid preparation vessel 15 and the other end being open. The nozzle 16 includes a retaining portion 61 and a discharging portion 62 which extend from one end side, where the nozzle 16 is bonded to the liquid preparation vessel 15, to the other end.

The retaining portion 61 is formed to be able to retain a reaction liquid generated by passing through a porous filter 63 and a first reagent sheet 64. More specifically, the retaining portion 61 is formed to have an inner diameter gradually decreasing from the porous filter 63 side to the discharging portion 62 side.

The retaining portion 61 includes the connection port 71 at the end portion on the liquid preparation vessel 15 side. The connection port 71 is formed to be able to be fitted to the to-be-connected port 51*c* of the second cylinder portion 51. More specifically, the connection port 71 includes the second edge portion 71*a* formed in an annular shape and the projection portion 71*b*. The projection portion 71*b* is formed to have an outer diameter almost equal to the inner diameter of the recess portion 51*e* provided for the to-be-connected portion Sic of the second cylinder portion 51.

The retaining portion 61 includes, on the inner circumferential surface of the end portion on the connection port 71 side, an abutment portion 72 which abuts against the porous filter 63. The abutment portion 72 is a large-diameter portion of the retaining portion 61, whose inner circumferential surface is formed to have a larger diameter than the remaining inner circumferential surfaces of the retaining portion 61.

The retaining portion 61 includes, in part of the wall portion, a fourth through-hole portion 73 exposed to the outside. The fourth through-hole portion 73 is formed to be located above the level of a solution moving from the retaining portion 61 to the discharging portion 62 when the discharging portion 62 faces down. The fourth through-hole portion 73 is also formed to be located above the level of a reaction liquid retained inside the retaining portion 61 when the discharging portion 62 faces up. The fourth through-hole portion 73 is sealed by a first sealing member 74 which does not allow moisture to permeate and allows only air to permeate. When the discharging portion 62 faces down, the fourth through-hole portion 73 can prevent a reduction in the internal pressure of the nozzle 16 efficiently. Therefore a reaction liquid would be discharged from the nozzle 16 quickly. In addition, when the discharging portion 62 faces up, an increase in internal pressure of the first cylinder portion 14 with a reduction in the volume of the first cylinder portion 14 and an increase in internal pressure of the second cylinder portion 51 with a reduction in the volume of the second cylinder portion 51 would be suppressed by discharging of air through the fourth through-hole portion 73. Note that a plurality of fourth through-hole portions 73 may be provided.

The discharging portion 62 has an orifice 62*a*. The orifice 62*a* is formed to have an inner diameter almost equal to the outer diameter of each projection portion 83*b* provided for a reception port 83 of a test cartridge 17. In addition, the orifice 62*a* is formed to have an outer diameter smaller than the inner diameter of a partition portion 83*c* provided for the reception port 83. Furthermore, the orifice 62*a* is formed to be able to be inserted until it abuts against a liquid reception portion 83*d* provided for the reception port 83. The orifice 62*a* can be sealed by a second sealing member 62*b* which does not allow moisture to permeate and allows only air to permeate, or by an impermeable material. This sealing member can be attached by means including ultrasonic welding, heat sealing, adhesive, or other.

The porous filter 63 is formed to be accommodated in the abutment portion 72. More specifically, the porous filter 63 is formed into a columnar shape with an outer diameter larger than the inner diameter of the abutment portion 72. A thermosetting resin material is used for the porous filter 63. The porous filter 63 is pressed into the abutment portion 72 and abuts against the inner circumferential surface of the abutment portion 72. In addition, the porous filter 63 abuts against the principal surface of the abutment portion 72 through the first reagent sheet 64.

The first reagent sheet 64 is a sheet-like member to which a dried first reagent is fixed. The first reagent sheet 64 is formed into a circular shape with an outer diameter almost equal to that of the porous filter 63. The first reagent sheet 64 is stacked on the porous filter 63. The porous filter 63 is accommodated in the abutment portion 72 such that the first reagent sheet 64 faces the discharging portion 62 side.

Note that the dead volume of the sample liquid preparing apparatus 1 may be adjusted from the capacity of a reaction liquid which flows in and the mixing ratio between a sample and a sample process liquid.

Figure 10:
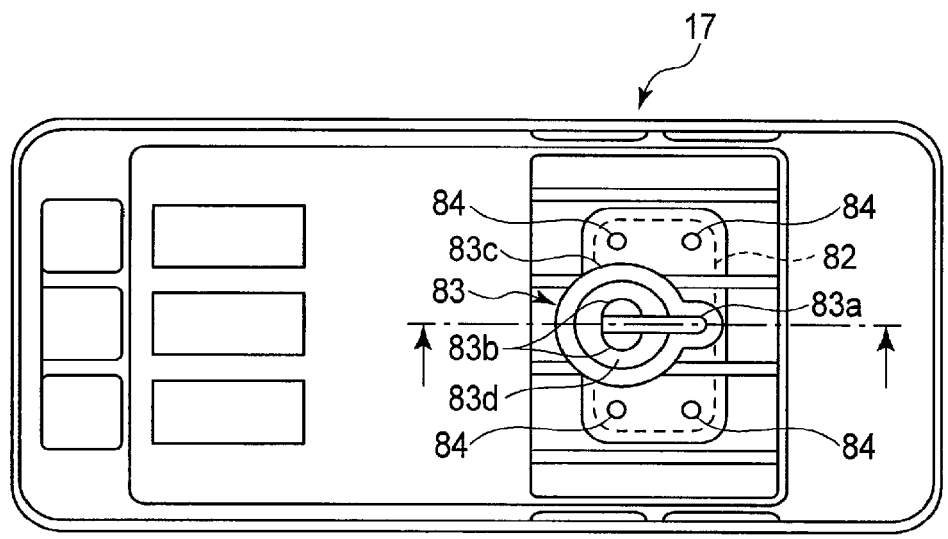
FIG. 10 is a top view showing the arrangement of a test cartridge constituting a test kit together with the sample liquid preparing apparatus shown in FIG. 1.

FIG. 10 is a top view showing the arrangement of the test cartridge 17 which constitutes the test kit together with the sample liquid preparing apparatus 1 according to the embodiment. FIG. 11 is a sectional view showing the arrangement of the test cartridge 17.

The test cartridge 17 constitutes the test kit together with the sample liquid preparing apparatus 1. The test cartridge 17 includes a reaction chamber 82 formed in the test cartridge 17 represented by a broken line in FIG. 10. The reaction chamber 82 is formed to have a long side in the widthwise direction of the test cartridge 17 and a short side in the depth direction of the test cartridge 17. A bottom portion of the reaction chamber 82 is formed by a transparent member 81. The surface of the transparent member 81 in the reaction chamber 82 side is coated with a second reagent. In the test cartridge 17, the reaction liquid which flows into the reaction chamber 82 reacts with the second reagent. The reaction state of the reaction liquid in the test cartridge 17 is analyzed based on the reflecting state of light that has entered to the transparent member 81. The test cartridge 17 includes, on the upper surface of the reaction chamber 82, the reception port 83 which causes a reaction liquid discharged from the sample liquid preparing apparatus 1 to flow into the reaction chamber 82 and a plurality of fifth through-hole portions 84 which discharge air corresponding to the reaction liquid inflowing from the reception port 83. The fifth through-hole portions 84 are, for example, provided at the four corners of the upper surface of the test cartridge 17 symmetrically with respect to a reception slit portion 83a provided in the reception port 83.

The reception port 83 is formed to be able to be fitted to the orifice 62a of the sample liquid preparing apparatus 1. The reception port 83 includes the reception slit portion 83a, the projection portions 83b, the partition portion 83c, and a liquid reception portion 83d. The reception slit portion 83a is formed to extend in the short-side direction so as to have its center at the middle position of the long side and the middle position of the short side. The reception slit portion 83a is formed to have a length that does not exceed the length of the short side of the reaction chamber 82. More specifically, the reception slit portion 83a is formed to have a length almost equal to the distance between the fifth through-hole portions 84 arranged along the short side of the reaction chamber 82. The reception slit portion 83a is formed in a width suitable to produce a capillary action. If the width of the reception slit portion 83a is too narrow, the reaction liquid will not flow into the reaction chamber 82 through the reception port 83. Note that if the width of the reception slit portion 83a is too wide, the reaction liquid retained in the reaction chamber 82 will leak out from the reaction chamber 82 through the reception port 83.

The projection portions 83b are formed to be able to tear apart the second sealing member 62b which seals the orifice 62a of the sample liquid preparing apparatus 1 and to allow a reaction liquid to flow out from the orifice 62a and into the reaction chamber 82. More specifically, the projection portions 83b are two semi-conical projections separated from each other by the reception slit portion 83a between them. The projection portions 83b are formed such that the total width of the projection portions 83b and the reception slit portion 83a is almost equal to the inner diameter of the orifice 62a of the sample liquid preparing apparatus 1 on the principal surface of the liquid reception portion 83d. Note that the projection portions 83b may be two semi-columnar projections separated from each other by the reception slit portion 83a between them.

The partition portion 83c is formed to be able to prevent a reaction liquid flowing out from the orifice 62a of the sample liquid preparing apparatus 1 from flowing out to the outside of the reception port 83. More specifically, the partition portion 83c is formed to have a predetermined height with respect to the liquid reception portion 83d and surround the reception slit portion 83a and the projection portions 83b.

The liquid reception portion 83d is formed to have a predetermined width around the projection portions 83b. The liquid reception portion 83d abuts against the orifice 62a provided for the discharging portion 62 of the nozzle 16 when a reaction liquid flows in from the sample liquid preparing apparatus 1.

A method of preparing a reaction liquid by using the sample liquid preparing apparatus 1 and causing the prepared reaction liquid to flow into the test cartridge 17 will be described next with reference to FIGS. 12, 13, 14, 15, 16, 17, 18, 19, 20, 21, 22, and 23.

First of all, the user grips the sample collection unit 11. At this time, the sample collection unit 11 is in a state in which part of the first cylinder portion 14 is accommodated in the cap portion 13, and the first columnar portion 41b provided for the first to-be-fixed portion 41 of the first cylinder portion 14 is fixed by the first fixing portion 21e provided for the first guide portion 21b of the outer portion 21. In addition, the second columnar portion 42b provided for the second to-be-fixed portion 42 of the first cylinder portion 14 is fixed to an end portion of the fifth slit portion 52d provided for the second guide portion 21c of the outer portion 21. The user then brings the capillary portion 31a into contact with a body fluid S such as whole blood, as shown in FIG. 12. The internal pressure of the first cylinder portion 14 balances with the atmospheric pressure via the first and second through-hole portions 31g and 31h. For this reason, the body fluid S is collected as a sample by the capillary portion 31a by a capillary action.

Figure 13:
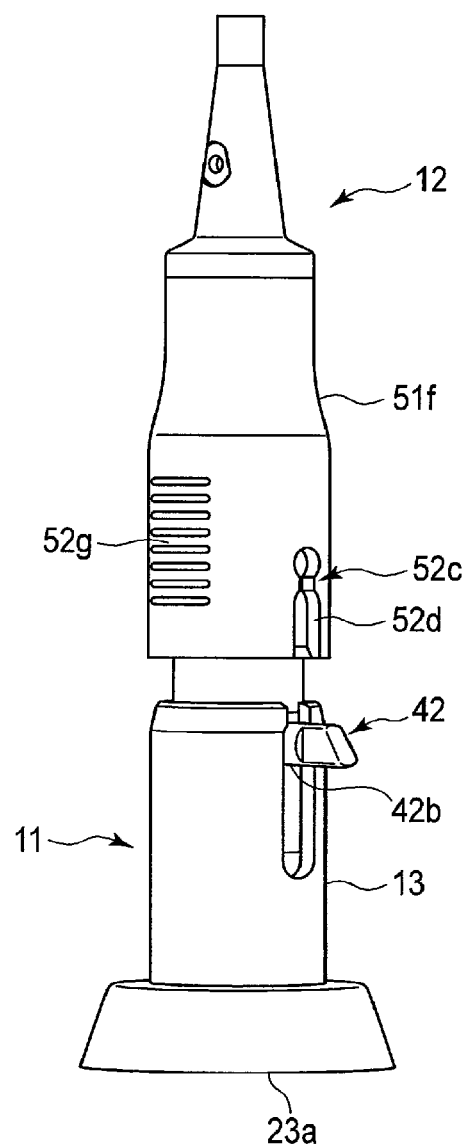
FIG. 13 is a perspective view showing a case in which the sample collection unit is accommodated in a sample liquid preparing unit.

Upon collecting the sample, the user makes the first planar portion 23a provided for the cap portion 13 of the sample collection unit 11 abut against a flat surface like the surface of a desk. This makes the sample collection unit 11 self-stand, with the capillary portion 31a facing up. The user matches the direction of the second to-be-fixed portion 42 of the sample collection unit 11 with the direction of the third guide portion 52c of the sample liquid preparing unit 12 so as to allow the second to-be-fixed portion 42 of the sample collection unit 11 to move along the third guide portion 52c of the sample liquid preparing unit 12. The user puts the sample liquid preparing unit 12 on the sample collection unit 11 which self-stands, with the capillary portion 31a facing up, as shown in FIG. 13.

The user grips the second grip portion 52g of the sample liquid preparing unit 12 and pushes the sample liquid preparing unit 12 toward the sample collection unit 11. At this time, the user pushes the sample liquid preparing unit 12 toward the sample collection unit 11 while the second columnar portion 42b of the second to-be-fixed portion 42 of the sample collection unit 11 is accommodated in the fifth slit portion 52d of the third guide portion 52c of the sample liquid preparing unit 12.

When the user pushes the sample liquid preparing unit 12 toward the sample collection unit 11, the first cylinder portion 14 of the sample collection unit 11 is inserted into the second cylinder portion 51 of the sample liquid preparing unit 12. More specifically, first of all, the first seal portion 31c of the sealing member 31b abuts against the inner circumferential surface of the second cylinder portion 51. The second cylinder portion 51 is pushed toward the sample collection unit 11 while the first seal portion 31c of the sealing member 31b abuts and seals against the inner circumferential surface of the second cylinder portion 51. Subsequently, the second seal portion 31d of the sealing member 31b abuts against the inner circumferential surface of the second cylinder portion 51. The second cylinder portion 51 is pushed toward the sample collection unit 11 while the first seal portion 31c and the second seal portion 31d abut and seal against the inner circumferential surface of the second cylinder portion 51.

When the user pushes the sample liquid preparing unit 12 toward the sample collection unit 11, the tapered portion 52b of the sample liquid preparing unit 12 comes into contact with the first to-be-guided portion 41c of the first to-be-fixed portion 41 of the sample collection unit 11, as shown in FIG. 14. The user grips the second grip portion 52g of the sample liquid preparing unit 12 and pushes the sample liquid preparing unit 12 toward the sample collection unit 11. Subsequently, the first to-be-guided portion 41c receives a stress in the central direction of the sample collection unit 11 from the tapered portion 52b, and the first beam portion 41a of the first to-be-fixed portion 41 of the sample collection unit 11 flexes in the central direction. This releases the first columnar portion 41b of the first to-be-fixed portion 41 of the first cylinder portion 14 from the first fixing portion 21e of the first guide portion 21b of the outer portion 21.

Figure 16:
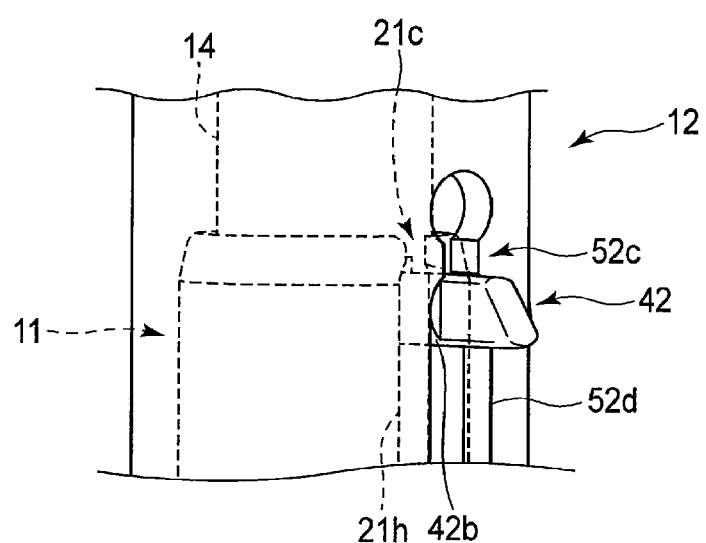
FIG. 16 is an enlarged view of the second to-be-fixed portion and the third guide portion shown in FIG. 15.

Subsequently, when the user pushes the sample liquid preparing unit 12 toward the sample collection unit 11, the second columnar portion 42b of the second to-be-fixed portion 42 of the sample collection unit 11 comes into contact with the end portion of the fifth slit portion 52d of the third guide portion 52c of the sample liquid preparing unit 12, as shown in FIG. 15. At this time, as shown in FIG. 16, the second columnar portion 42b comes into contact with the end portion of the fifth slit portion 52d of the third guide portion 52c and the end portion of the fourth slit portion 21h of the second guide portion 21c. The second columnar portion 42b comes into contact with the end portion of the fifth slit portion 52d of the third guide portion 52c to limit the sample liquid preparing unit 12 from being pushed against the first cylinder portion 14 of the sample collection unit 11.

When the user pushes the sample liquid preparing unit 12 toward the sample collection unit 11 while the second columnar portion 42b is in contact with the end portion of the fifth slit portion 52d of the third guide portion 52c, the first to-be-fixed portion 41 released from the first fixing portion 21e of the first guide portion 21b is accommodated in the second slit portion 21f of the first to-be-guided portion 41c. When the user further pushes the sample liquid preparing unit 12 toward the sample collection unit 11, the first to-be-guided portion 41c moves toward the cap portion 13 along the second slit portion 21f upon movement of the sample liquid preparing unit 12 toward the sample collection unit 11. This action releases the lock between the cap and the first cylinder, allowing the cap to push the plugs 34 and 35 toward the bypass channel. At this time, the second columnar portion 42b of the second to-be-fixed portion 42 moves toward the cap portion 13 along the fourth slit portion 21h of the second guide portion 21c.

When the user pushes the sample liquid preparing unit 12 toward the sample collection unit 11 while the second columnar portion 42b is in contact with the end portion of the fifth slit portion 52d of the third guide portion 52c, the plunger portion 22 of the cap portion 13 of the sample collection unit 11 pushes the second plug 35 accommodated in the first cylinder portion 14 in the front end direction of the first cylinder portion 14. When the second plug 35 is pushed in the front end direction of the first cylinder portion 14, the first plug 34 is pushed in the front end direction of the first cylinder portion 14 by a low-compressibility sample process liquid sealed by the inner circumferential surface of the first cylinder portion 14, the first plug 34, and the second plug 35.

When the user pushes the sample liquid preparing unit 12 toward the sample collection unit 11, the third seal portion 34a and the fourth seal portion 34b of the first plug 34 reach positions falling between the first through-hole portion 31g and the second through-hole portion 31h provided for the front end portion 31 of the first cylinder portion 14, as shown in FIG. 17. At this time, a flow channel F shown in FIG. 29 is opened, which is formed from the first through-hole portion 31g, the gap between the outer circumferential surface of the first cylinder portion 14 and the inner circumferential surface of the second cylinder portion 51, which face each other through the window portion 31e of the sealing member 31b, and the second through-hole portion 31h.

When the user pushes the sample liquid preparing unit 12 toward the sample collection unit 11 while the flow channel F is open, the plunger portion 22 of the sample collection unit 11 pushes the second plug 35 in the front end direction of the first cylinder portion 14. This causes a sample process liquid sealed by the first plug 34 and the second plug 35 to flow into a space R1 between the inside end face of the first cylinder portion 14 and the end face of the first plug 34 which is located on the front end side of the first cylinder portion 14 through the flow channel F. The sample process liquid keeps flowing into the space R1 until the second plug 35 comes into contact with the first plug 34 and the first plug 34 and the second plug 35 close the first through-hole portion 31g and the second through-hole portion 31h, as shown in FIG. 18.

When the user pushes the sample liquid preparing unit 12 toward the sample collection unit 11 while the first plug 34 is in contact with the second plug 35, the plunger portion 22 of the sample collection unit 11 pushes the first plug 34 and the second plug 35 together in the front end direction of the first cylinder portion 14. This reduces the volume of the space R1. As shown in FIG. 19, with a reduction in the volume of the space R1, the sample process liquid retained in the space R1 reaches the capillary portion 31a and is dispensed into a space R2 between the inside end face of the second cylinder portion 51 and the outside end face of the first cylinder portion 14 while washing out the sample collected by the capillary portion 31a. In this instance, since the center of the capillary portion 31a is more apart from the axis of the first cylinder portion 14 than the outer circumferential surface of the cylindrical projection portion 34c of the first plug 34, the first plug 34 will not clog the capillary portion 31a even when the inner end face of the first cylinder 14 and the first plug 34 contact each other.

Since the third through-hole portion 51b is formed at a position facing the capillary portion 31a through the axis of the first cylinder portion 14, even if a sample process liquid rushes from the capillary portion 31a into the space R2, the rushing sample process liquid does not directly come into contact with the porous filter 63 accommodated in the nozzle 16. That is, the porous filter 63 will not get wet by the sample process liquid rushing into the space R2. In addition, the sample process liquid dispensed from the capillary portion 31a contacts the outside end face of the first cylinder portion 14 to generate a turbulent flow. This turbulent flow uniformly mixes the sample process liquid with the sample washed out of the capillary portion 31a by the sample process liquid, thereby promoting reaction between the sample process liquid and the sample. A liquid obtained by mixing a sample with a sample process liquid will be referred to as a sample liquid mixture.

Note that if the capacity of the space R2 is sufficiently large with respect to the capacity of a sample liquid mixture, the position of the second columnar portion 42b of the second to-be-fixed portion 42 and the positions of the first and second through-holes portion 31g and 31h formed in the first cylinder portion 14 may be adjusted in accordance with the capacity of the space R2. That is, the capacity of the space R2 does not depend on the capacity of a sample liquid mixture. The capacity of a sample liquid mixture is decided by a mixing ratio (dilution ratio) with a sample.

The user pushes the sample liquid preparing unit 12 toward the sample collection unit 11 until the inside end face of the first cylinder portion 14 abuts against the end face of the first plug 34 which is located on the front end side of the first cylinder portion 14. When the inside end face of the first cylinder portion 14 abuts against the end face of the first plug 34 which is located on the front end side of the first cylinder portion 14, the user cannot further push the sample liquid preparing unit 12 toward the sample collection unit 11. When the inside end face of the first cylinder portion 14 abuts against the end face of the first plug 34 which is located on the front end side of the first cylinder portion 14, the first to-be-guided portion 41c of the first to-be-fixed portion 41 comes into contact with the end portion of the first guide portion 21b of the second slit portion 21f which is located on the pedestal portion 23 side. In addition, the second columnar portion 42b of the second to-be-fixed portion 42 comes into contact with the end portion of the fourth slit portion 21h of the second guide portion 21c which is located on the pedestal portion 23 side. In this state, the sample liquid mixture does not mix with the first reagent unless the user intentionally removes the limitation on the second columnar portion 42b of the second to-be-fixed portion 42 and pushes the sample liquid preparing unit 12 toward the sample collection unit 11. Note that if a time lapse must occur to facilitate the reaction between the sample processing liquid and the sample, it is possible to leave them standing for a while and wait until the reaction sufficiently progresses.

Subsequently, as shown in FIG. 20, the user pushes the second to-be-guided portion 42c of the second to-be-fixed portion 42 in the central direction while gripping the second grip portion 52g of the first accommodation portion 52. The second beam portion 42a of the second to-be-fixed portion 42 of the sample collection unit 11 flexes in the central direction because of the pressing force applied by the user in the central direction. This releases the second columnar portion 42b of the second to-be-fixed portion 42 from the end portion of the fifth slit portion 52d of the first accommodation portion 52 of the liquid preparation vessel 15. When the second columnar portion 42b of the second to-be-fixed portion 42 is released, the user pushes the sample liquid preparing unit 12 toward the sample collection unit 11 again while gripping the second grip portion 52g.

Figure 21:
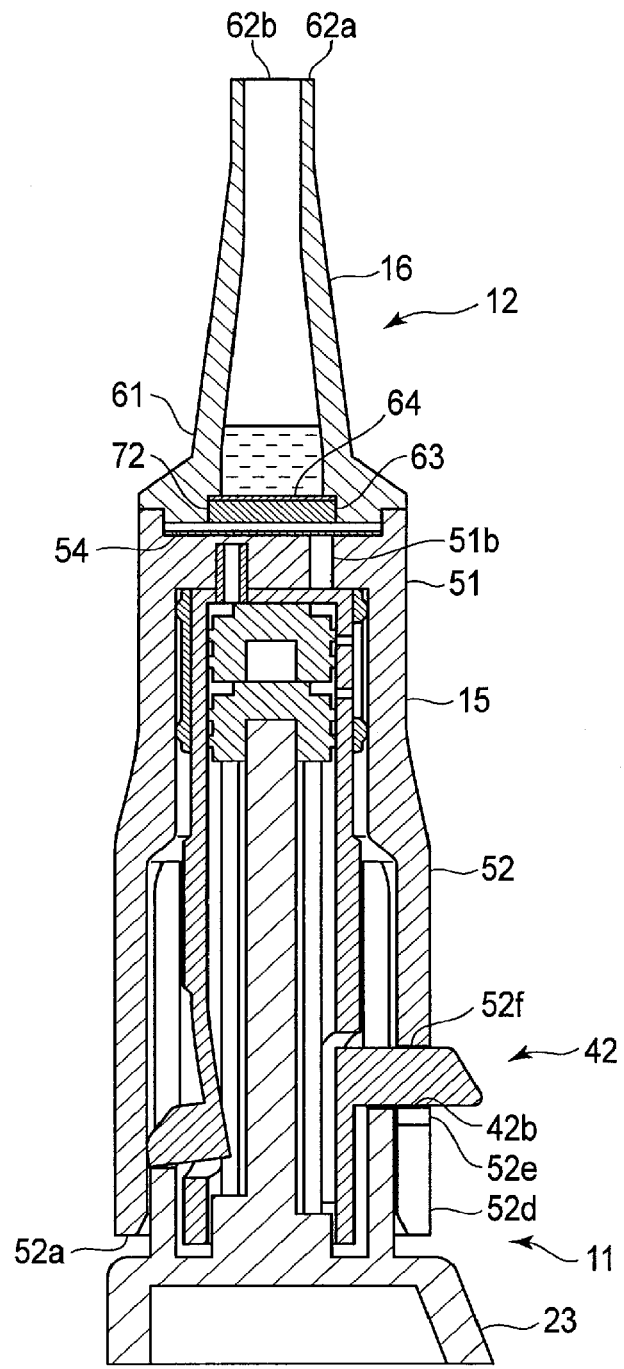
FIG. 21 is a sectional view showing a case in which the outer end face of the first cylinder portion abuts against the inner end face of the second cylinder portion.

When the user pushes the sample liquid preparing unit 12 toward the sample collection unit 11 when the second columnar portion 42b of the second to-be-fixed portion 42 is released, the released second to-be-guided portion 42c of the second to-be-fixed portion 42 is accommodated in the sixth slit portion 52e. When the user further pushes the sample liquid preparing unit 12 toward the sample collection unit 11, the second to-be-guided portion 42c moves along the sixth slit portion 52e along with the movement of the sample liquid preparing unit 12 toward the sample collection unit 11. The second columnar portion 42b of the second to-be-fixed portion 42 reaches the terminal fixing portion 52f of the first accommodation portion 52 of the liquid preparation vessel 15 and is fixed by the terminal fixing portion 52f, as shown in FIG. 22. When the second columnar portion 42b of the second to-be-fixed portion 42 reaches the terminal fixing portion 52f of the first accommodation portion 52, the third opening portion 52a of the liquid preparation vessel 15 reaches near the principal surface of the pedestal portion 23 of the cap portion 13, as shown in FIG. 21.

Along with the movement of the sample liquid preparing unit 12 when the second to-be-guided portion 42c of the second to-be-fixed portion 42 moves along the sixth slit portion 52e and the second columnar portion 42b reaches the terminal fixing portion 52f of the first accommodation portion 52, a sample liquid mixture retained in the space R2 flows out from the third through-hole portion 51b provided in the second cylinder portion 51 of the liquid preparation vessel 15. The sample liquid mixture flows into the retaining portion 61 of the nozzle 16 through a hole formed in the second cylinder portion 51.

The sample liquid mixture flowing into the retaining portion 61 comes into contact with the porous filter 63 held by the abutment portion 72 of the retaining portion 61 and infiltrates the porous filter 63. The sample liquid mixture which has infiltrated the porous filter 63 comes into contact with the first reagent sheet 64 to which the first reagent is fixed. The first reagent fixed to the first reagent sheet 64 elutes into the sample liquid mixture when the sample liquid mixture passes through the first reagent sheet 64. The sample liquid mixture into which the first reagent has eluted is called a reaction liquid. The reaction liquid is retained in the retaining portion 61, as shown in FIG. 21. The reaction liquid is temporarily retained in the retaining portion 61 to uniformly mix the first reagent with the sample liquid mixture. At this time, the first sealing member 74 which seals the fourth through-hole portion 73 and the second sealing member 62b which seals the orifice 62a discharge air to the outside. This provides a balance between the internal pressure of the nozzle 16 and the atmospheric pressure and suppresses an increase in internal pressure even with reductions in the volumes of the nozzle 16 and the second cylinder portion 51.

Subsequently, the user orients the sample liquid preparing apparatus 1 to direct the discharging portion 62 of the nozzle 16 downward and thrusts the orifice 62a of the discharging portion 62 into the projection portions 83b provided for the reception port 83 of the test cartridge 17, as shown in FIG. 23. In this manner, by turning the sample liquid preparing apparatus 1 upside down, the reaction between the sample liquid mixture and the first reagent in the reaction liquid will be further promoted. The projection portions 83b tear apart the second sealing member 62b which seals the orifice 62a. The user pushes the sample liquid preparing apparatus 1 toward the test cartridge 17 until the orifice 62a abuts against the liquid reception portion 83d of the reception port 83. This fits the orifice 62a of the sample liquid preparing apparatus 1 to the reception port 83 of the test cartridge 17. The reaction liquid retained in the retaining portion 61 of the nozzle 16 flows out from the orifice 62a through the torn second sealing member 62b. At this time, the first sealing member 74 which seals the fourth through-hole portion 73 takes in air from the outside. This suppresses a reduction in the internal pressure of the nozzle 16 and continues to discharge the reaction liquid until all the reaction liquid retained in the nozzle 16 is discharged.

The reaction liquid flowing out from the orifice 62a flows into the reaction chamber 82 from the reception slit portion 83a of the reception port 83 using a capillary action. In addition, the reaction liquid flowing out from the orifice 62a is held back by the partition portion 83c of the reception port 83 so as not to flow out to the outside of the reception port 83, and is gathered by the liquid reception portion 83d to flow into the reaction chamber 82 from the reception slit portion 83a. In the reaction chamber 82, the amount of air corresponding to the flowing reaction liquid is exhausted from the fifth through-hole portions 84. This operation can prevent the increase of internal pressure of the reaction chamber 82 generated with a compression of the air volume in the reaction chamber 82. Accordingly, the reaction liquid continues to flow into the reaction chamber 82 until it becomes full. That is, the reaction liquid will equally spread in every part in the reaction chamber 82. When the reaction liquid flows into the reaction chamber 82, the reaction liquid comes into contact with the surface of the transparent member 81 in the reaction chamber 82 side and reacts with the second reagent.

As described above, the sample liquid preparing apparatus 1 according to this embodiment includes the sample collection unit 11 and the sample liquid preparing unit 12. The user puts the sample liquid preparing unit 12 on the sample collection unit 11 which has collected a sample, and then pushes the sample liquid preparing unit 12 toward the sample collection unit 11. The movement of the first and second plugs 34 and 35 accommodated in the sample collection unit 11 is limited when the first to-be-fixed portion 41 provided for the first cylinder portion 14 of the sample collection unit 11 is fixed to the first fixing portion 21e provided for the cap portion 13 of the sample collection unit 11. The fixation of the first to-be-fixed portion 41 is released when the third opening portion 52a of the liquid preparation vessel 15 of the sample liquid preparing unit 12 presses the first to-be-fixed portion 41. The movement of the first cylinder portion 14 with respect to the second cylinder portion 51 of the liquid preparation vessel 15 is limited when the end portion of the fifth slit portion 52d provided for the first accommodation portion 52 of the liquid preparation vessel 15 serves as a second fixing portion to fix the second to-be-fixed portion 42 provided for the first cylinder portion 14. The fixation of the second to-be-fixed portion 42 is released when the user presses the second to-be-fixed portion 42 after the second plug 35 abuts against the first plug 34, and the first plug 34 abuts against the inside end face of the first cylinder portion 14. This allows the sample liquid preparing apparatus 1 to promote the reaction of the sample in a stepwise manner.

The sample liquid preparing apparatus 1 according to this embodiment therefore can uniformly mix a sample with a sample process liquid and uniformly mix the liquid mixture of the sample and the sample process liquid with a first reagent.

In addition, in this embodiment, when the user pushes the sample liquid preparing unit 12 to the sample collection unit 11, the first cylinder portion 14 is pushed toward the cap portion 13, while the first to-be-fixed portion 41 provided for the first cylinder portion 14 is moved along the first guide portion 21b provided for the cap portion 13, and the second to-be-fixed portion 42 provided for the first cylinder portion 14 is moved along the second guide portion 21c provided for the cap portion 13. In addition, when the user pushes the sample liquid preparing unit 12 to the sample collection unit 11 after the fixation of the second to-be-fixed portion 42 by the fifth slit portion 52d provided for the first accommodation portion 52 of the liquid preparation vessel 15 is released, the second cylinder portion 51 is pushed toward the cap portion 13 along the sixth slit portion 52e provided for the first accommodation portion 52. With this operation, when the sample liquid preparing unit 12 is pushed to the sample collection unit 11, the sample liquid preparing apparatus 1 generates a reaction liquid.

In addition, in this embodiment, the orifice 62a provided for the discharging portion 62 of the nozzle 16 is sealed by the second sealing member 62b. When a reaction liquid is retained in the retaining portion 61 of the nozzle 16, the orifice 62a of the nozzle 16 of the sample liquid preparing apparatus 1 is directed downward and is fitted in the reception port 83 of the test cartridge 17. The second sealing member which seals the orifice 62a is torn apart by the projection portions 83b of the reception port 83. The reaction liquid retained in the nozzle 16 flows from the torn second sealing member 62b into the reaction chamber 82 through the reception slit portion 83a.

When using a conventional sample liquid preparing apparatus, after connecting the sample liquid preparing apparatus which has collected a sample to the test cartridge, the user grips the grip of the sample liquid preparing apparatus with one hand and grips the lower end of the sample liquid preparing apparatus connected to the test cartridge with the other hand. The user then injects the sample and a sample process liquid from the sample liquid preparing apparatus into the test cartridge by rotating the grip of the sample liquid preparing apparatus. However, since the sample liquid preparing apparatus is small, it is difficult for the user to grip the sample liquid preparing apparatus with both hands. The sample liquid preparing apparatus 1 according to this embodiment allows the user to connect the sample liquid preparing apparatus 1 to the test cartridge 17 with one hand. In addition, the sample liquid preparing apparatus 1 according to the embodiment allows the user to inject a reaction liquid into the test cartridge 17 by only placing the sample liquid preparing apparatus 1 into the reception port 83 of the test cartridge 17. That is, it is possible to inject a reaction liquid into the test cartridge 17 without any leakage of the reaction liquid without performing any additional operation such as rotating the grip.

In addition, in this embodiment, the third through-hole portion 51b provided for the second cylinder portion 51 of the liquid preparation vessel 15 of the sample liquid preparing unit 12 is formed at a position facing the capillary portion 31a through the axis of the first cylinder portion 14. A sample process liquid in the first cylinder portion 14 which is sealed by the first plug 34 and the second plug 35 contains a surfactant. For this reason, when air passes through the porous filter 63 after the sample process liquid comes into contact with the porous filter 63 and infiltrates it, air bubbles are generated. The sample liquid preparing apparatus 1 according to this embodiment prevents the dispensed sample process liquid from coming into direct contact with the porous filter 63 even when the sample process liquid gushes from the capillary portion 31*a*. This can prevent the porous filter 63 from generating air bubbles.

In addition, according to this embodiment, the second planar portion 23*b* provided on the pedestal portion 23 of the cap portion 13 of the sample collection unit 11 is formed in the same direction as that in which the capillary portion 31*a* is separated from the axis of the first cylinder portion 14. With this structure, even when the sample liquid preparing apparatus 1 overturns, its rotation stops at the second planar portion 23*b*, thereby preventing the sample process liquid from coming into contact with the porous filter 63.

Furthermore, in this embodiment, the film 54 covering the liquid preparation vessel 15 of the sample liquid preparing unit 12 has a minimal hole at a predetermined position excluding an edge portion bonded to the recess portion 51*e*. Since air vents first from the minimal hole because of the elasticity of the film 54, it is possible to suppress a sample liquid mixture of a sample and a sample process liquid from reaching the porous filter 63 before air reaches the porous filter 63. This can prevent the porous filter 63 from generating air bubbles.

Note that the above embodiment has exemplified the method of using the sample liquid preparing apparatus 1 when the first planar portion 23*a* provided for the cap portion 13 of the sample collection unit 11 is made to abut against a flat surface such as the surface of a desk. However, this is not exhaustive. The user may push the sample liquid preparing unit 12 to the sample collection unit 11 without placing the sample collection unit 11 on a flat surface.

Figure 26:
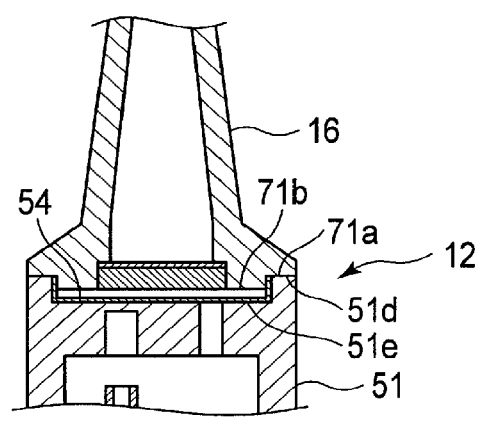
FIG. 26 is a sectional view showing still another example of attaching the film shown in FIG. 9.

In addition, the above embodiment has exemplified the case in which the film 54 is fixed to the recess portion 51*e* provided for the to-be-connected port 51*c* of the second cylinder portion 51 of the liquid preparation vessel 15 by using an adhesive agent or ultrasonic welding. However, this is not exhaustive. The film 54 may be fixed so as to be mechanically sandwiched between the liquid preparation vessel 15 and the nozzle 16. FIGS. 24, 25, and 26 are sectional views each showing an example of the sample liquid preparing apparatus 1 when the film 54 is mechanically fixed by the liquid preparation vessel 15 and the nozzle 16.

Referring to FIG. 24, the projection portion 71*b* provided for the connection portion 71 of the nozzle 16 is formed such that the distance from the principal surface of the second edge portion 71*a* provided for the connection port 71 to the principal surface of the projection portion 71*b* is slightly larger than the distance from the principal surface of the film 54 placed on the recess portion 51*e* to the principal surface of the first edge portion 51*d* provided for the to-be-connected port 51*c*. When the principal surface of the first edge portion 51*d* abuts against the principal surface of the second edge portion 71*a*, the projection portion 71*b* pushes the film 54 in the direction of the recess portion 51*e*. This makes the film 54 be sandwiched and fixed between the recess portion 51*e* and the projection portion 71*b*.

Referring to FIG. 25, the connection portion 71 of the nozzle 16 has, on the principal surface of the projection portion 71*b*, an annular projection portion 71*c* formed in an annular shape with a predetermined width. The annular projection portion 71*c* is formed such that the distance from the principal surface of the second edge portion 71*a* to the principal surface of the annular projection portion 71*c* is slightly larger than the distance from the principal surface of the film 54 placed on the recess portion 51*e* to the principal surface of the first edge portion 51*d*. When the principal surface of the first edge portion 51*d* abuts against the principal surface of the second edge portion 71*a*, the annular projection portion 71*c* pushes the film 54 in the direction of the recess portion 51*e*. This makes the film 54 be sandwiched and fixed between the recess portion 51*e* and the annular projection portion 71*c*.

Referring to FIG. 26, the projection portion 71*b* is formed to have an outer diameter slightly smaller than the inner diameter of the recess portion 51*e*. In other words, there is a gap between the outer circumferential surface of the projection portion 71*b* and the inner circumferential surface of the recess portion 51*e*. In this case, the film 54 is formed to have a diameter slightly smaller the inner diameter of the recess portion 51*e*. The film 54 is sandwiched and fixed between the outer circumferential surface of the projection portion 71*b* and the inner circumferential surface of the recess portion 51*e*. Fixing the film 54 in the manner shown in FIGS. 24, 25, and 26 can make the film 54 be mechanically fixed between the liquid preparation vessel 15 and the nozzle 16 while bonding the principal surface of the first edge portion 51*d* to the principal surface of the second edge portion 71*a* by ultrasonic welding.

Figure 27:
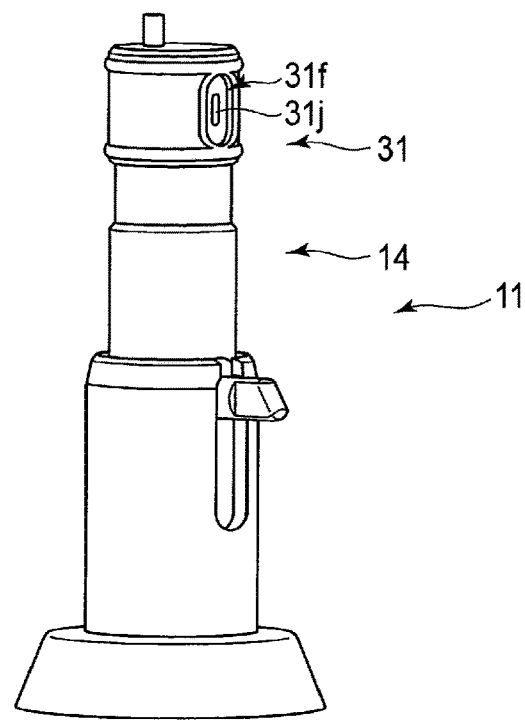
FIG. 27 is a perspective view showing another example of the bypass portion shown in FIG. 4.
Figure 28:
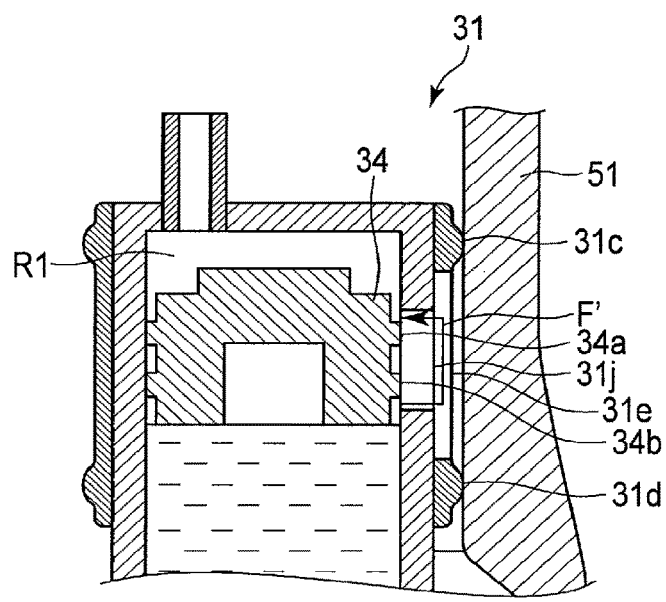
FIG. 28 is a sectional view showing the arrangement of a sample liquid preparing unit including the bypass portion shown in FIG. 27.

The above embodiment has been described with reference to an example, where the bypass portion 31*f* provided in the front end portion 31 has the first through-hole portion 31*g* and the second through-hole portion 31*h*. This is, however, not a limitation. As shown in FIG. 27, the bypass portion 31*f* may be provided with a slit-like through-hole portion 31*j* that extends in the axis direction of the first cylinder portion 14. FIG. 28 is a sectional view showing the arrangement of the sample liquid preparing unit 12 when the bypass portion 31*f* has a slit-like through-hole portion 31*j*. The slit-like through-hole portion 31*j* is formed to have a length in the axial direction that is larger than the length between the upper end of the third seal portion 34*a* and the lower end of the fourth seal portion 34*b* of the first plug 34, as shown in FIG. 28.

With the length of the slit-like through-hole portion 31*j* being larger than the length between the upper end of the third seal portion 34*a* and the lower end of the fourth seal portion 34*b*, the third seal portion 34*a* and the fourth seal portion 34*b* reach the positions covered by the slit-like through-hole portion 31*j* when the sample liquid preparing unit 12 is pushed toward the sample collection unit 11, as shown in FIG. 28. At this time, a flow channel F' is opened, which is formed from the slit-like through-hole portion 31*j*, and the gap between the outer circumferential surface of the first cylinder portion 14 and the inner circumferential surface of the second cylinder portion 51, which face each other through the window portion 31*e* of the sealing member 31*b*. When the sample liquid preparing unit 12 is pushed toward the sample collection unit 11 while the flow channel F' is open, the plunger portion 22 of the sample collection unit 11 pushes the second plug 35 in the front end direction of the first cylinder portion 14. This causes a sample process liquid sealed by the first plug 34 and the second plug 35 to flow into a space R1 between the inside end face of the first cylinder portion 14 and the end face of the first plug 34 which is located on the front end side of the first cylinder portion 14 through the flow channel F'. The sample process liquid keeps flowing into the space R1 until the second plug 35 comes into contact with the first plug 34, and the first plug 34 and the second plug 35 close the slit-like through-hole portion 31*j*.

Also, with the bypass portion 31*f* having the slit-like through-hole portion 31*j*, air mixed into the sample process liquid is trapped in the portion enclosed by the third seal portion 34*a* and the fourth seal portion 34*b* via the slit-like through-hole portion 31*j*. The air mixed into the sample process liquid is thereby prevented from being conveyed upward. Note that the slit-like through-hole portion 31*j* may be formed to cover the third seal portion 34*a* and the fourth seal portion 34*b* when the inner end face of the first cylinder 14 and the cylindrical projection portion 34*c* of the first plug 34 contact each other. This can minimize the dead volume of the sample liquid preparing apparatus 1.

In addition, the above embodiment has exemplified the case in which the nozzle 16 accommodates the porous filter 63 and the first reagent sheet 64. However, this is not exhaustive. A liquid reagent may be sealed in a tearable bag such as a film bag, instead of the porous filter 63 and the first reagent sheet 64, and the sealing bag may be accommodated in the retaining portion 61 of the nozzle 16. In this case, a movable needle for tearing apart the sealing bag accommodated in the retaining portion 61 is installed in the second hole portion 51*a* provided for the second cylinder portion 51 of the liquid preparation vessel 15 of the sample liquid preparing unit 12. When the sample liquid preparing unit 12 is pushed to the sample collection unit 11 and the capillary portion 31*a* provided for the front end portion 31 of the first cylinder portion 14 is accommodated in the second hole portion 51*a*, the lower end of the movable needle is pushed upward by the front end of the capillary portion 31*a*. When the lower end of the movable needle is pushed upward, the needle provided on the front end of the movable needle reaches the sealing bag and tears it apart. When the sealing bag is torn apart, a liquid reagent flows out from the sealing bag into the retaining portion 61, and the sample liquid mixture flowing from the third through-hole portion 51*b* is mixed with the liquid reagent in the retaining portion 61.

An embodiment of the present invention has been described above. However, this embodiment is presented merely as an example and is not intended to restrict the scope of the invention. The embodiment can be carried out in various other forms, and various omissions, replacements, and alterations can be made without departing from the spirit of the invention. The embodiment and its modifications are also incorporated in the scope and the spirit of the invention as well as in the invention described in the claims and their equivalents.

The invention claimed is:

1. A sample liquid preparing apparatus comprising:
   a first cylinder portion having a first to-be-fixed portion and a second to-be-fixed portion and configured to accommodate a first plug and a second plug between which a liquid is sealed;
   a cap portion provided to be configured to accommodate the first cylinder portion and including a plunger portion configured to push the second plug and a first fixing portion configured to limit the plunger portion from pushing the second plug by fixing the first to-be-fixed portion; and
   a liquid preparation vessel provided to be configured to accommodate the first cylinder portion and the cap portion and including a second cylinder portion whose internal space is pressed by the first cylinder portion and a second fixing portion configured to limit the first cylinder portion from pushing by fixing the second to-be-fixed portion,
   wherein the internal space is maintained while the second fixing portion limits the first cylinder portion from pushing by fixing the second to-be-fixed portion.

2. The sample liquid preparing apparatus of claim 1, wherein the liquid preparation vessel includes a contact portion which comes into contact with the fixed first to-be-fixed portion when the first cylinder portion is pushed to the second cylinder portion,
   the first to-be-fixed portion is released from the first fixing portion by a stress received from the contact portion, and
   the second to-be-fixed portion is released from the second fixing portion by an external force.

3. The sample liquid preparing apparatus of claim 2, wherein the first to-be-fixed portion has a round portion which receives the stress.

4. The sample liquid preparing apparatus of claim 1, wherein the first to-be-fixed portion is provided on an opening end side of the first cylinder portion with respect to the second to-be-fixed portion.

5. The sample liquid preparing apparatus of claim 1, wherein the first cylinder portion includes a capillary portion configured to collect a sample on an end face at a front end at a position separated from an axis of the first cylinder portion by a predetermined distance.

6. The sample liquid preparing apparatus of claim 5, wherein
   the first plug includes a cylindrical projection portion at a position facing an inner end face of the first cylinder portion, and
   a distance between a center of the capillary portion and the axis of the first cylinder portion is larger than a distance between an outer circumferential surface of the cylindrical projection portion and the axis of the first cylinder portion.

7. The sample liquid preparing apparatus of claim 5, further comprising a nozzle bonded to an end face of the liquid preparation vessel at a front end,
   wherein the liquid preparation vessel has a through-hole portion in an end face bonded to the nozzle, and
   the through-hole portion is formed at a position facing the capillary portion through an axis of the first cylinder portion.

8. The sample liquid preparing apparatus of claim 7, wherein the liquid preparation vessel has the through-hole portion covered by a film in which a hole is formed.

9. The sample liquid preparing apparatus of claim 7, wherein an orifice of the nozzle is sealed by a sealing member which does not allow moisture to permeate and allows air to permeate.

10. The sample liquid preparing apparatus of claim 1, wherein the plunger portion of the cap portion includes a core portion inserted into the second plug.

11. The sample liquid preparing apparatus of claim 1, wherein the cap portion includes a planar portion formed along an axis of the cap portion.

12. The sample liquid preparing apparatus of claim 11, wherein the first cylinder portion includes a capillary portion configured to collect a sample on an end face at a front end at a position separated from an axis of the first cylinder portion by a predetermined distance, and
   the cap portion includes the planar portion in the same direction in which the capillary portion is separated from the axis of the first cylinder portion.

13. The sample liquid preparing apparatus of claim 1, wherein the first plug includes first and second seal portions which contact an inner circumferential surface of the first cylinder portion to seal a gap between the inner circumferential surface of the first cylinder portion and the first plug, the first cylinder portion includes an axially extending slit-like through-hole portion, and the slit-like through-hole portion has a length larger than a distance between outer end faces of the first and second seal portions.

14. The sample liquid preparing apparatus of claim 1, wherein the first cylinder portion includes a capillary portion configured to collect a sample on an end face at a front end, the cap portion includes a first guide portion configured to guide movement of the first to-be-fixed portion whose fixation by the first fixing portion is released and a second guide portion configured to guide movement of the second to-be-fixed portion, and pushes the second plug with the plunger portion until the first to-be-fixed portion reaches an end portion of the first guide portion and the second to-be-fixed portion reaches an end portion of the second guide portion, the liquid preparation vessel includes an opening end which comes into contact with the first to-be-fixed portion fixed by the first fixing portion and provides an interference with the first to-be-fixed portion to release fixation by the first fixing portion when the first cylinder portion is pushed to the second cylinder portion, the internal space in which the sample flowing out from the capillary portion when the plunger portion pushes the second plug is mixed with a sample process liquid as the liquid, a third guide portion configured to guide movement of the second to-be-fixed portion whose fixation by the second fixing portion is released, and a through-hole portion from which the sample and the sample process liquid mixed in the internal space are pushed out as a sample liquid mixture by the first cylinder portion whose second to-be-fixed portion is guided by the third guide portion, and the apparatus further comprises a nozzle bonded to an end face of the liquid preparation vessel at a front end, loaded with a first reagent, and including a retaining portion configured to generate a reaction liquid by mixing the sample liquid mixture pushed out from the through-hole portion with the first reagent and an orifice configured to discharge the reaction liquid, wherein the orifice being sealed by a sealing member which does not allow moisture to permeate and allows air to permeate.

15. A test kit comprising:

a sample liquid preparing apparatus defined in claim 14; and a test cartridge in which a reaction liquid discharged from the sample liquid preparing apparatus is injected, the test cartridge comprising:

a reception slit portion configured to make the reaction liquid flow therein, and a projection portion including projections separated by the reception slit portion and configured to tear apart the sealing member sealing the orifice with the projections and cause the reaction liquid flowing out from the orifice through the torn sealing member to flow into the reception slit portion.

16. The kit of claim 15, wherein the reception slit portion has a width to produce a capillary action.

17. A sample liquid preparing method comprising:

collecting a sample from a front end of a first cylinder portion;

putting a liquid preparation vessel including a second cylinder portion on the first cylinder portion while a cap portion including a plunger portion is connected to the first cylinder portion, wherein the plunger portion being configured to push a movable plug accommodated in the first cylinder portion, and an internal space of the second cylinder being pressed by the first cylinder portion;

mixing a sample process liquid sealed in the first cylinder portion with the collected sample collected from the front end of the first cylinder portion in the internal space of the second cylinder portion by causing the plunger portion to push the movable plug; and generating a reaction liquid by mixing the sample liquid mixture mixed in the second cylinder portion with a first reagent loaded into a nozzle in a retaining portion in the nozzle, wherein the sample liquid mixture being pushed out to the nozzle by causing the first cylinder portion to push the second cylinder portion, and wherein the internal space is maintained while the second fixing portion limits the first cylinder portion from pushing by fixing the second to-be-fixed portion.

* * * * *